US012728119B2

(12) United States Patent
Kim

(10) Patent No.: US 12,728,119 B2
(45) Date of Patent: Sep. 8, 2026

(54) PHARMACEUTICAL COMPOSITION FOR PREVENTING OR TREATING CANCER COMPRISING 3-KETOACYL CoA THIOLASE INHIBITOR AND CARNITINE ACYLCARNITINE CARRIER INHIBITOR

(71) Applicant: NATIONAL CANCER CENTER, Goyang-si (KR)

(72) Inventor: Sooyoul Kim, Goyang-si (KR)

(73) Assignee: NEW CANCER CURE-BIO CO., LTD., Goyang-si (KR)

( * ) Notice: Subject to any disclaimer, the term of this patent is extended or adjusted under 35 U.S.C. 154(b) by 826 days.

(21) Appl. No.: 18/004,009

(22) PCT Filed: Jul. 1, 2021

(86) PCT No.: PCT/KR2021/008362

§ 371 (c)(1),
(2) Date: Dec. 30, 2022

(87) PCT Pub. No.: WO2022/005228

PCT Pub. Date: Jan. 6, 2022

(65) Prior Publication Data

US 2023/0255947 A1 Aug. 17, 2023

(30) Foreign Application Priority Data

Jul. 1, 2020 (KR) ........................ 10-2020-0080973

(51) Int. Cl.
*A61K 31/495* (2006.01)
*A61K 31/194* (2006.01)
(Continued)

(52) U.S. Cl.
CPC .......... *A61K 31/4439* (2013.01); *A61K 45/06* (2013.01); *A61P 35/00* (2018.01)

(58) Field of Classification Search
CPC .. A61K 31/4439; A61K 45/06; A61K 31/337; A61K 31/437; A61K 31/4745;
(Continued)

(56) References Cited

U.S. PATENT DOCUMENTS 10,676,490 B2 6/2020 Dingra et al.
2010/0285001 A1 11/2010 Land et al.
(Continued)

FOREIGN PATENT DOCUMENTS

KR 10-2019-0099245 8/2019
KR 10-2020-0041806 4/2020

OTHER PUBLICATIONS

Vander Linden C and Corbet C, (2019), Therapeutic Targeting of Cancer Stem Cells: Integrating and Exploiting the Acidic Niche, Front. Oncol. 9:159 (Year: 2019).*
(Continued)

*Primary Examiner* — Jeffrey S Lundgren
*Assistant Examiner* — Paul Randall Gauger
(74) *Attorney, Agent, or Firm* — Oblon, McClelland, Maier & Neustadt, L.L.P.

(57) ABSTRACT

A pharmaceutical composition tor preventing treating cancer including a 3-ketoacyl CoA thiolase (ACAA) inhibitor and a carat in acylcarnitine carrier (CAC) inhibitor represented by Formula 1 below:

[Formula 1]

(Continued)

where $R_1$ to $R_4$ are each independently H, $C_{1-6}$ alkyl substituted or unsubstituted with one or more halogen, or $C_{1-6}$ alkoxy substituted or unsubstituted with one or more halogen, and where the halogen is selected from F, Cl, Br, and I.

9 Claims, 30 Drawing Sheets

(51) Int. Cl.

| | |
|---|---|
| ***A61K 31/4439*** | (2006.01) |
| ***A61K 38/02*** | (2006.01) |
| ***A61K 39/395*** | (2006.01) |
| ***A61K 45/06*** | (2006.01) |
| ***A61K 47/10*** | (2017.01) |
| ***A61K 47/26*** | (2006.01) |
| ***A61P 35/00*** | (2006.01) |
| ***A61P 43/00*** | (2006.01) |
| ***C07F 5/02*** | (2006.01) |

(58) Field of Classification Search

CPC ................ A61K 31/495; A61K 31/513; A61K 31/7068; A61K 33/243; A61P 35/00

See application file for complete search history.

(56) References Cited

U.S. PATENT DOCUMENTS

2012/0082659 A1 4/2012 Land et al.
2012/0114670 A1 5/2012 Land et al.
2018/0194784 A1 7/2018 Dingra et al.
2020/0093737 A1 3/2020 Anlahr et al.
2020/0255455 A1 8/2020 Dingra et al.

OTHER PUBLICATIONS

Vander Linden C and Corbet C, (2019), Therapeutic Targeting of Cancer Stem Cells: Integrating and Exploiting the Acidic Niche, Front. Oncol. 9:159 (Year: 2019) (Year: 2019).*

Udelnow A, Kreyes A, Ellinger S, Landfester K, Walther P, et al. (2011), Omeprazole Inhibits Proliferation and Modulates Autophagy in Pancreatic Cancer Cells, PLoS ONE 6(5): e20143 (Year: 2011).*

Vander Linden C and Corbet C, (2019), Therapeutic Targeting of Cancer Stem Cells: Integrating and Exploiting the Acidic Niche, Front. Oneal. 9: 159 (Year: 2019) (Year: 2019) (Year: 2019).*

Udelnow A, Kreyes A, Ellinger S, Landfester K, Walther P, et al. (2011 ), Omeprazole Inhibits Proliferation and Modulates Autophagy in Pancreatic Cancer Cells, PLoS ONE 6(5): e20143 w (Year: 2011).*

Kantor, P. F. et al., "The Antianginal dmgdrug Trimetazidine Shifts Cardiac Energy Metabolism From Fatty Acid Oxidation to Glucose Oxidation by Inhibiting Mitochondrial Long-Chain 3-Ketoacyl Coenzyme A Thiolase," Circulation Research, Mar. 17, 2000; 2000; vol. 86, pp. 580-588.

International Search Report mailed on Oct. 13, 2021 in PCT/KR2021/008362 filed on Jul. 1, 2021 (3 pages).

* cited by examiner

PHARMACEUTICAL COMPOSITION FOR PREVENTING OR TREATING CANCER COMPRISING 3-KETOACYL CoA THIOLASE INHIBITOR AND CARNITINE ACYLCARNITINE CARRIER INHIBITOR

CROSS REFERENCE TO RELATED APPLICATIONS

This application is a National Stage entry under 35 U.S.C. § 371 of PCT/KR2021/008362, filed on Jul. 1, 2021, and claims priority to Korean Patent Application No. 10-2020-0080973, filed on Jul. 1, 2020. The entire contents of both are incorporated herein by reference.

TECHNICAL FIELD

The present invention relates to a pharmaceutical composition for preventing or treating cancer, or an anticancer adjuvant, comprising a 3-ketoacyl CoA thiolase inhibitor and a Carnitine Acylcarnitine Carrier inhibitor.

BACKGROUND ART

Normal cells are capable of regular and elastic proliferation and inhibition as needed, whereas cancer cells proliferate indefinitely, which is a cell mass composed of undifferentiated cells, also called tumor. These cancer cells invade the surrounding tissues and metastasize to other organs in the body, causing severe pain and eventually death. Despite advances in medicine, the number of cancer patients in Korea has increased continuously and has increased by about 44% over the past 10 years.

There were first-generation anticancer agents, chemical anticancer agents, and second-generation, targeted anti-cancer agents. In order to overcome side effects thereof, immuno-oncology agents have been developed as third-generation anti-cancer agents, and research is being conducted continuously. However, the biggest problem in current cancer treatment is the recurrence of cancer because there are various mutations in the cancer, making it difficult to target a specific cancer, and resistance to the anticancer drugs used in the treatment of relapsed cancer occurs. After all, even after treating the primary cancer, most of the patients die due to metastasis and recurrent cancer. Accordingly, in order to enhance the effect of anticancer drugs, a strategy for combining anticancer drugs and treating them in combination has been proposed.

Trimetazidine, a 3-ketoacyl CoA thiolase (ACAA) inhibitor, is an anti-ischemic (anti-angina) metabolizer or fatty acid oxidation inhibitor, and is known to have an effect of improving myocardial glucose utilization by inhibiting fatty acid metabolism.

Omeprazole, a Carnitine Acylcarnitine Carrier (CAC) inhibitor, is a proton-pump inhibitor and is known to be effective in treating gastroesophageal reflux disease, peptic ulcer, erosive esophagitis or eosinophilic esophagitis.

Korean Patent Laid-Open Patent No. 10-2020-0041806 discloses a pharmaceutical composition for preventing or treating cancer comprising a malate-aspartate shuttle inhibitor and carnitine acylcarnitine carrier inhibitor, and it is described that the types of carnitine acylcarnitine carrier inhibitor include trimetazidine or omeprazole.

However, a study or description of whether an anticancer effect can be obtained by using a 3-ketoacyl CoA thiolase (ACAA) inhibitor and a carnitine acylcarnitine carrier (CAC) inhibitor in combination has not been disclosed.

DISCLOSURE

Technical Problem

Accordingly, the present inventors have made intensive efforts to provide a combination anticancer agent capable of significantly inhibiting cancer cells, and as a result, when a 3-ketoacyl CoA thiolase inhibitor and a carnitine acylcarnitine carrier inhibitor were treated in combination, it was confirmed that the cancer cell inhibitory effect was significantly increased compared to the case where each inhibitor was treated alone, and the present invention was completed.

Therefore, an object of the present invention is to provide a pharmaceutical composition for preventing or treating cancer, or an anti-cancer adjuvant comprising a 3-ketoacyl CoA thiolase inhibitor and a carnitine acylcarnitine carrier inhibitor.

Technical Solution

In order to achieve the above object, the present invention provides a pharmaceutical composition for preventing or treating cancer comprising a 3-ketoacyl CoA thiolase (ACAA) inhibitor and a Carnitine Acylcarnitine Carrier (CAC) inhibitor represented by Formula 1 below:

[Formula 1]

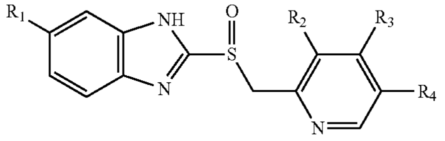

wherein, $R_1$ to $R_4$ are each independently H, $C_{1-6}$ alkyl substituted or unsubstituted with one or more halogen, or $C_{1-6}$ alkoxy substituted or unsubstituted with one or more halogen, and wherein halogen is selected from the group consisting of F, Cl, Br, and I.

In addition, the present invention provides an anticancer adjuvant comprising a 3-ketoacyl CoA thiolase (ACAA) inhibitor and a Carnitine Acylcarnitine Carrier (CAC) inhibitor represented by Formula 1 above.

The ACAA inhibitor may be trimetazidine (KN713), ranolazine (KN715), or a pharmaceutically acceptable salt thereof.

The CAC inhibitor may be omeprazole (KN510), lansoprazole (KN511), pantoprazole (KN512), or a pharmaceutically acceptable salt thereof.

The ACAA inhibitor and the CAC inhibitor may be included in a concentration ratio of 1:100 to 100:1.

The ACAA inhibitor and the CAC inhibitor may be administered sequentially or simultaneously.

The cancer may include one or more selected from the group consisting of colon cancer, lung cancer, stomach cancer, breast cancer, brain cancer, melanoma, glioblastoma, prostate cancer, ovarian cancer, kidney cancer, pancreatic cancer, blood cancer, and liver cancer.

The pharmaceutical composition or anticancer adjuvant may further include an additional anticancer agent.

The additional anticancer agent may be irinotecan, paclitaxel, capecitabine (5-fu), gemcitabine, vemurafenib, or a pharmaceutically acceptable salt thereof.

In addition, the present invention provides a method for preventing or treating cancer comprising administering or taking a composition comprising a 3-ketoacyl CoA thiolase (ACAA) inhibitor and a Carnitine Acylcarnitine Carrier (CAC) inhibitor represented by Formula 1 above as an active ingredient to an individual.

In addition, the present invention provides a use of a composition for preventing or treating cancer comprising a 3-ketoacyl CoA thiolase (ACAA) inhibitor and a Carnitine Acylcarnitine Carrier (CAC) inhibitor represented by Formula 1 above as an active ingredient.

Advantageous Effects

The present composition comprising a 3-ketoacyl CoA thiolase and a carnitine acylcarnitine carrier inhibitor can be provided as an effective combination anticancer agent because the growth of cancer cells, oxygen consumption and tumor size are significantly reduced compared to when a 3-ketoacyl CoA thiolase or a carnitine acylcarnitine carrier inhibitor is used alone, respectively.

DESCRIPTION OF DRAWINGS

FIG. 7*e* shows the results of analyzing the effect of the combined treatment of the CAC inhibitor KN512 (Pantoprazole) and the ACAA inhibitor KN715 (Ranolazine).

MODE OF THE INVENTION

Figure 1:
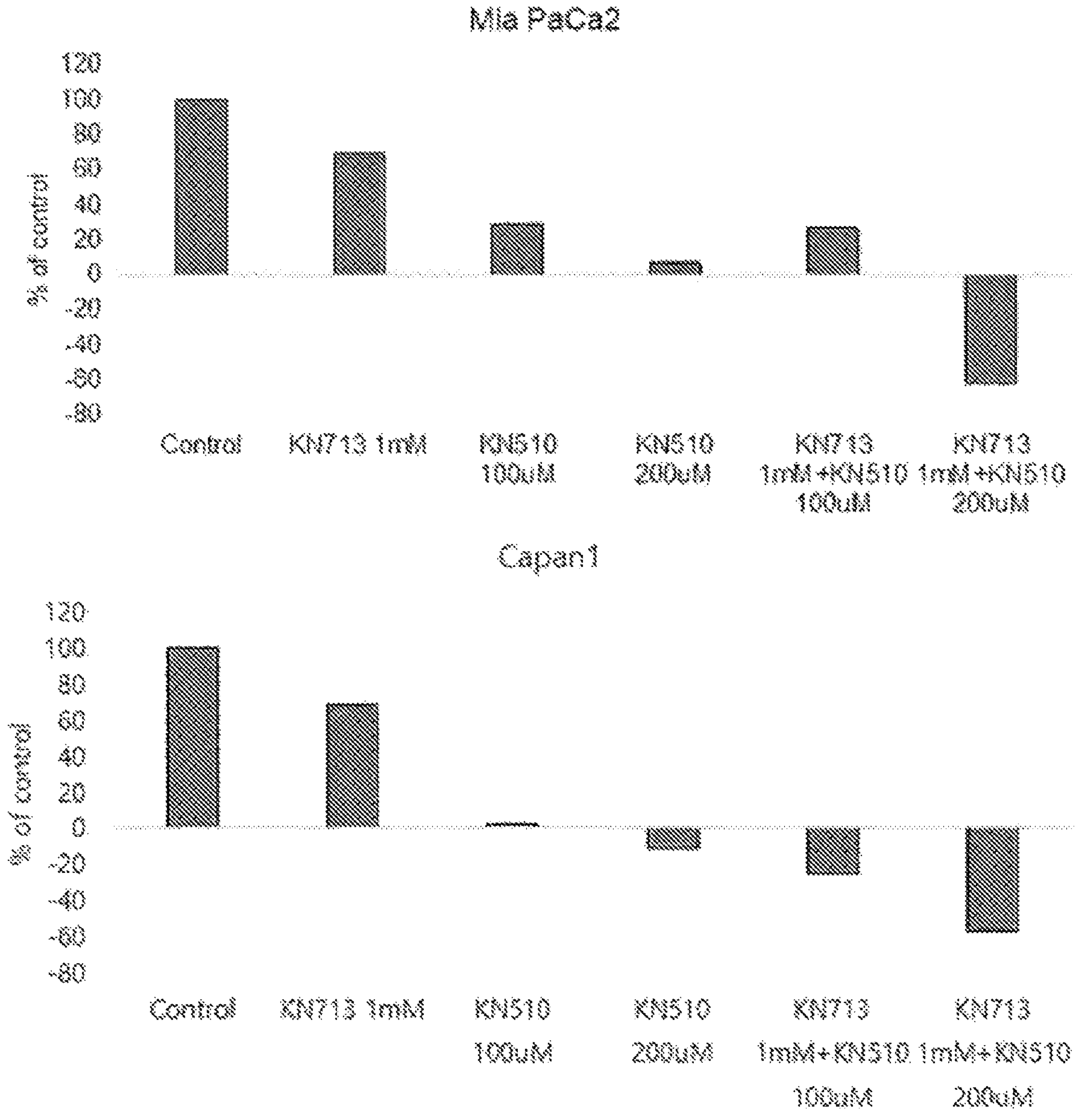
FIG. 1 shows the growth inhibitory effect of a cell line treated with trimetazidine (KN713) and/or omeprazole (KN510) on pancreatic cancer cell lines (MIA PaCa2 and Capan1). It was confirmed that the growth of the cell line was significantly inhibited when treated in combination with trimetazidine and omeprazole compared to the case where trimetazidine or omeprazole was treated alone.
Figure 2:
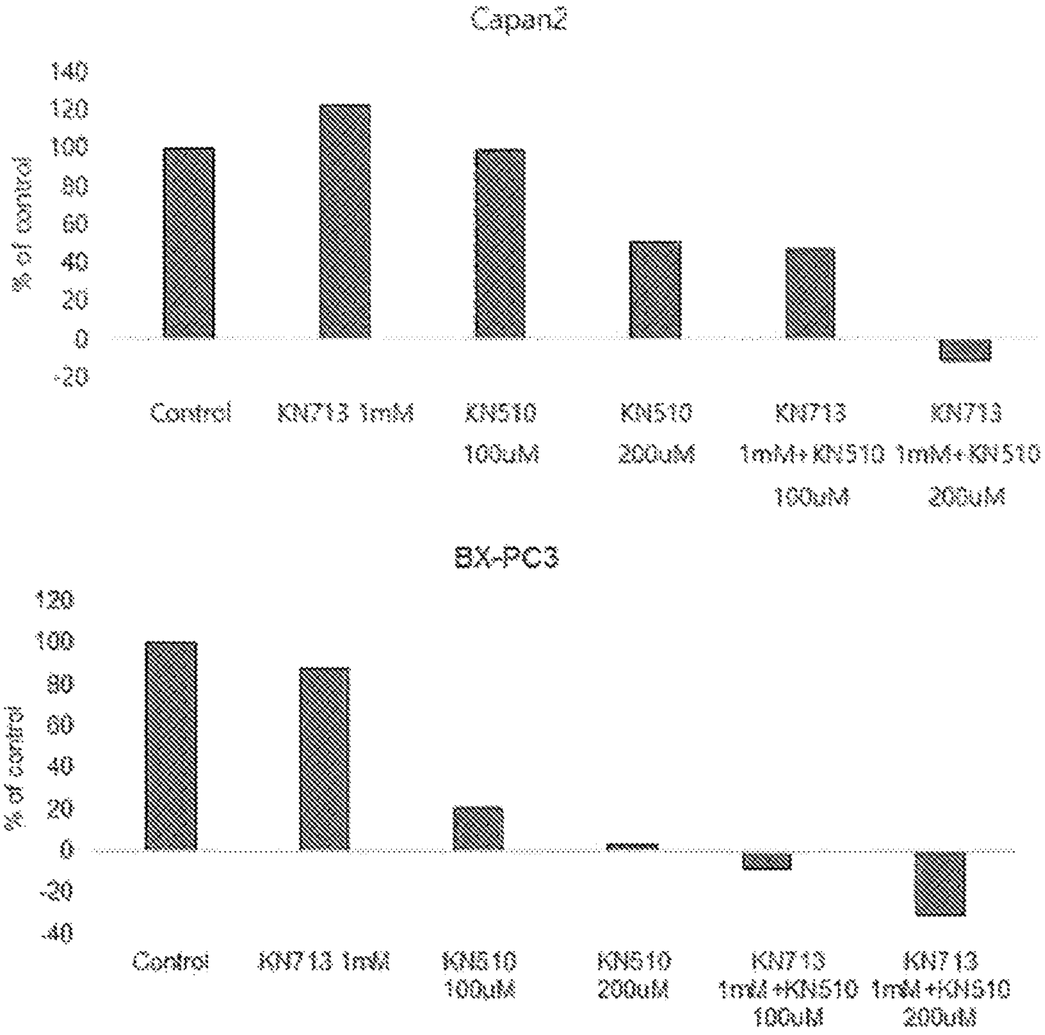
FIG. 2 shows the growth inhibitory effect of cell lines treated with trimetazidine (KN713) and/or omeprazole (KN510) on pancreatic cancer cell lines (Capan2 and BxPC-3). It was confirmed that the growth of the cell line was significantly inhibited when treated in combination with trimetazidine and omeprazole compared to the case where trimetazidine or omeprazole was treated alone.

Hereinafter, the present invention will be described in more detail.

As described above, the conventional anticancer drugs used for cancer treatment have problems in that side effects and drug resistance are likely to occur, so the development of anticancer targeted therapeutics as an alternative thereto is required.

The present composition comprising a 3-ketoacyl CoA thiolase and a carnitine acylcarnitine carrier inhibitor can be provided as an effective combination anticancer agent because the growth of cancer cells, oxygen consumption and tumor size are significantly reduced compared to when a 3-ketoacyl CoA thiolase or a carnitine acylcarnitine carrier inhibitor is used alone, respectively.

Accordingly, the present invention provides a pharmaceutical composition for preventing or treating cancer comprising a 3-ketoacyl CoA thiolase (ACAA) inhibitor and a Carnitine Acylcarnitine Carrier (CAC) inhibitor represented by Formula 1 below:

[Formula 1]

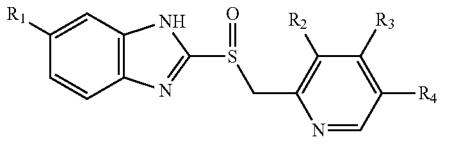

wherein, $R_1$ to $R_4$ are each independently H, $C_{1-6}$ alkyl substituted or unsubstituted with one or more halogen, or $C_{1-6}$ alkoxy substituted or unsubstituted with one or more halogen, and wherein halogen is selected from the group consisting of F, Cl, Br, and I.

The ACAA inhibitor may be trimetazidine (KN713), ranolazine (KN715), or a pharmaceutically acceptable salt thereof.

The CAC inhibitor may be omeprazole (KN510), lansoprazole (KN511), pantoprazole (KN512), or a pharmaceutically acceptable salt thereof.

The ACAA inhibitor and the CAC inhibitor may be included in a concentration ratio of 1:100 to 100:1.

The ACAA inhibitor and the CAC inhibitor may be administered sequentially or simultaneously.

The cancer may be selected from the group consisting of colon cancer, lung cancer, stomach cancer, breast cancer, brain cancer, melanoma, glioblastoma, prostate cancer, ovarian cancer, kidney cancer, pancreatic cancer, blood cancer, and liver cancer.

The composition of the present invention may be in various oral or parenteral formulations. When formulating the composition, it can be formulated using one or more buffers (e.g., saline or PBS), antioxidants, bacteriostatic agents, chelating agents (e.g., EDTA or glutathione), fillers, bulking agents, binders, adjuvants (e.g., aluminum hydroxide), suspending agent, thickening agent, wetting agents, disintegrating agents or surfactants, diluents or excipients.

Solid preparations for oral administration include tablets, pills, powders, granules, capsules, etc., and such solid preparations include at least one excipient in one or more compounds, for example, starch (corn starch, wheat starch, rice starch, potato starch, etc.), calcium carbonate, sucrose, lactose, dextrose, sorbitol, mannitol, xylitol, erythritol maltitol, cellulose, methyl cellulose, sodium carboxymethylcellulose and hydroxypropylmethyl-cellulose or gelatin are mixed and prepared. For example, tablets or dragees can be obtained by blending the active ingredient with a solid excipient, grinding it, adding suitable adjuvants, and processing it into a granular mixture.

In addition to simple excipients, lubricants such as magnesium stearate and talc may be also used. Liquid formulations for oral administration include suspensions, internal solutions, emulsions, or syrups. In addition to commonly used simple diluents such as water and liquid paraffin, various excipients such as wetting agents, sweetening agents, fragrances or preservatives may be included. In addition, in some cases, cross-linked polyvinylpyrrolidone, agar, alginic acid or sodium alginate may be added as a disintegrant, and an anti-aggregant, lubricant, wetting agent, flavoring agent, emulsifier and preservative may be additionally included.

The formulations for parenteral administration include sterile aqueous solutions, non-aqueous solutions, suspensions, emulsions, lyophilized formulations, or suppositories. For non-aqueous solvents and suspensions, propylene glycol, polyethylene glycol, vegetable oils such as olive oil, and injectable esters such as ethyl oleate may be used. As a base of the suppository, witepsol, macrogol, tween 61, cacao butter, laurin fat, glycerol, gelatin, etc. can be used.

The composition of the present invention may be administered orally or parenterally, and when administered parenterally, for external use; It can be formulated according to a method known in the art in the form of an injection for intraperitoneal, rectal, intravenous, intramuscular, subcutaneous, intrauterine dural or intracerebrovascular injection.

In the case of the injection, it must be sterilized and protected from contamination of microorganisms such as bacteria and fungi. For injection, examples of suitable carriers may include, but are not limited to, water, ethanol, polyols (e.g., glycerol, propylene glycol and liquid polyethylene glycol, etc.), mixtures thereof, and/or a solvent or dispersion medium containing vegetable oil. More preferably, suitable carriers, such as, Hanks' solution, Ringer's solution, phosphate buffered saline (PBS) or sterile water for injection with triethanolamine, isotonic solutions such as 10% ethanol, 40% propylene glycol and 5% dextrose. etc. can be used. In order to protect the injection from microbial contamination, it may further include various antibacterial and antifungal agents such as parabens, chlorobutanol, phenol, sorbic acid, thimerosal, and the like. In addition, in most cases, the injection may further contain an isotonic agent such as sugar or sodium chloride.

The composition of the present invention can be administered in a pharmaceutically effective amount. A pharmaceutically effective amount means an amount sufficient to treat a disease with a reasonable benefit/risk ratio applicable to medical treatment, and the effective dose level refers to the patient's disease type, severity, drug activity, drug sensitivity, and administration time, route of administration and excretion rate, duration of treatment, factors including concomitant drugs, and other factors well known in the medical field. The composition of the present invention may be administered as an individual therapeutic agent or in combination with other therapeutic agents, may be administered sequentially or simultaneously with conventional therapeutic agents, and may be administered single or multiple. That is, the total effective amount of the composition of the present invention may be administered to a patient as a single dose, and may be administered by a fractionated treatment protocol in which multiple doses are administered for a long period of time. In consideration of all of the above factors, it is important to administer an amount that can obtain the maximum effect with a minimum amount without side effects, which can be easily determined by those skilled in the art.

The preferred dosage of the composition varies depending on the patient's condition, body weight, degree of disease, drug form, administration route and period, but may be appropriately selected by those skilled in the art, for example, 0.0001 to 2,000 mg/kg per day, more preferably, it may be administered at 0.001 to 2,000 mg/kg. Administration may be administered once a day, or may be administered in several divided doses. However, the scope of the present invention is not limited by the dosage.

The composition of the present invention may be used alone or in combination with methods using surgery, radiation therapy, hormone therapy, chemotherapy, and biological response modifiers.

When cancer cell lines were treated with the present pharmaceutical composition comprising a 3-ketoacyl CoA thiolase and a carnitine acylcarnitine carrier inhibitor for preventing or treating cancer, a significantly increased cancer cell suppression effect can be obtained compared to when a 3-ketoacyl CoA thiolase or a carnitine acylcarnitine carrier inhibitor is used alone, respectively. In this case, the control used for comparison of the cancer cell suppression effect may be a medium treated with a vehicle solvent, and the vehicle may be DW (1%), DMSO (0.1% to 0.2%) or SMSO (0.1%).

In addition, the present invention can provide an anticancer adjuvant comprising a 3-ketoacyl CoA thiolase (ACAA) inhibitor and a Carnitine Acylcarnitine Carrier (CAC) inhibitor represented by Formula 1 above.

The ACAA inhibitor may be trimetazidine (KN713), ranolazine (KN715), or a pharmaceutically acceptable salt thereof.

The CAC inhibitor may be omeprazole (KN510), lansoprazole (KN511), pantoprazole (KN512), or a pharmaceutically acceptable salt thereof.

The ACAA inhibitor and the CAC inhibitor may be included in a concentration ratio of 1:100 to 100:1.

The ACAA inhibitor and the CAC inhibitor may be administered sequentially or simultaneously.

The cancer may be selected from the group consisting of colon cancer, lung cancer, stomach cancer, breast cancer, brain cancer, melanoma, glioblastoma, prostate cancer, ovarian cancer, kidney cancer, pancreatic cancer, blood cancer, and liver cancer.

The anticancer adjuvant of the present invention refers to any form for enhancing the anticancer effect of an anticancer agent or suppressing or improving the side effects of an anticancer agent. The anticancer adjuvant of the present invention may be administered in combination with various types of anticancer agents or anticancer adjuvants, and when administered in combination, even if the anticancer agent is administered at a level lower than the dose of a conventional anticancer agent, the same level of anticancer therapeutic effect can be exhibited, so safer anti-cancer treatment can be performed.

The administration route of the anticancer adjuvant may be administered through any general route as long as it can reach the target tissue. The anticancer adjuvant of the present invention may be administered intraperitoneally, intravenously, intramuscularly, subcutaneously, orally, intrapulmonary administration, or rectal, depending on the purpose, but is not limited thereto. In addition, the anticancer adjuvant may be administered by any device capable of transporting an active substance to a target cell.

The anticancer adjuvant of the present invention may be preferably formulated as an anticancer adjuvant by including one or more pharmaceutically acceptable carriers in addition to the active ingredient for administration. Carriers, excipients or diluents that may be included in the anticancer adjuvant of the present invention include lactose, dextrose, sucrose, sorbitol, mannitol, xylitol, erythritol, maltitol, starch, gum acacia, alginate, gelatin, calcium phosphate, Calcium Silicate, Cellulose, Methyl Cellulose, microcrystalline Cellulose, polyvinyl pyrrolidone, water, methyl hydroxybenzoate, propyl hydroxybenzoate, talc, magnesium stearate and mineral oil, but is not limited thereto.

The anticancer adjuvant of the present invention may be a formulation for oral or parenteral administration, and the description of the formulation is substituted for the description of the formulation of the pharmaceutical composition.

Hereinafter, the present invention will be described in more detail through examples. These examples are only for illustrating the present invention, and it is obvious to those of ordinary skill in the art that the scope of the present invention is not to be construed as being limited by these examples.

Example 1

SRB Analysis 1

Pancreatic cancer (MIA PaCa2, Capan1, Capan2, BxPC-3, SNU-213 or SNU-324) cell lines (100 μl) were seeded into 96-well microtiter plates at densities ranging from 7,500 to 10,000 cells/well depending on the doubling time of each cell line. After adding Trimetazidine (KN713) 1 mM, omeprazole (KN510) 100 or 200 μM, trimetazidine 1 mM+omeprazole 100 μM, trimetazidine 1 mM+omeprazole 200 μM, respectively, to each well by 100 μl each, and plate was incubated in a $CO_2$ incubator, and cold TCA was added to terminate the assay. 50 μl of cold 50% (w/v) TCA (final concentration: 10% TCA) was gently added to fix the cells and incubated at 4° C. for 60 minutes. The supernatant was discarded and the plate was washed 5 times with tap water and then air dried. A solution of 0.4% (w/v) Sulforhodamine B (100 μl) in 1% acetic acid was added to each well, and the plate was left at room temperature for 10 minutes. After staining, the plates were air dried after washing 5 times with 1% acetic acid to remove unbound dye. The bound dye was then solubilized with 10 mM trizma base and the absorbance was recorded at 515 nm using an automated plate reader.

Figure 3:
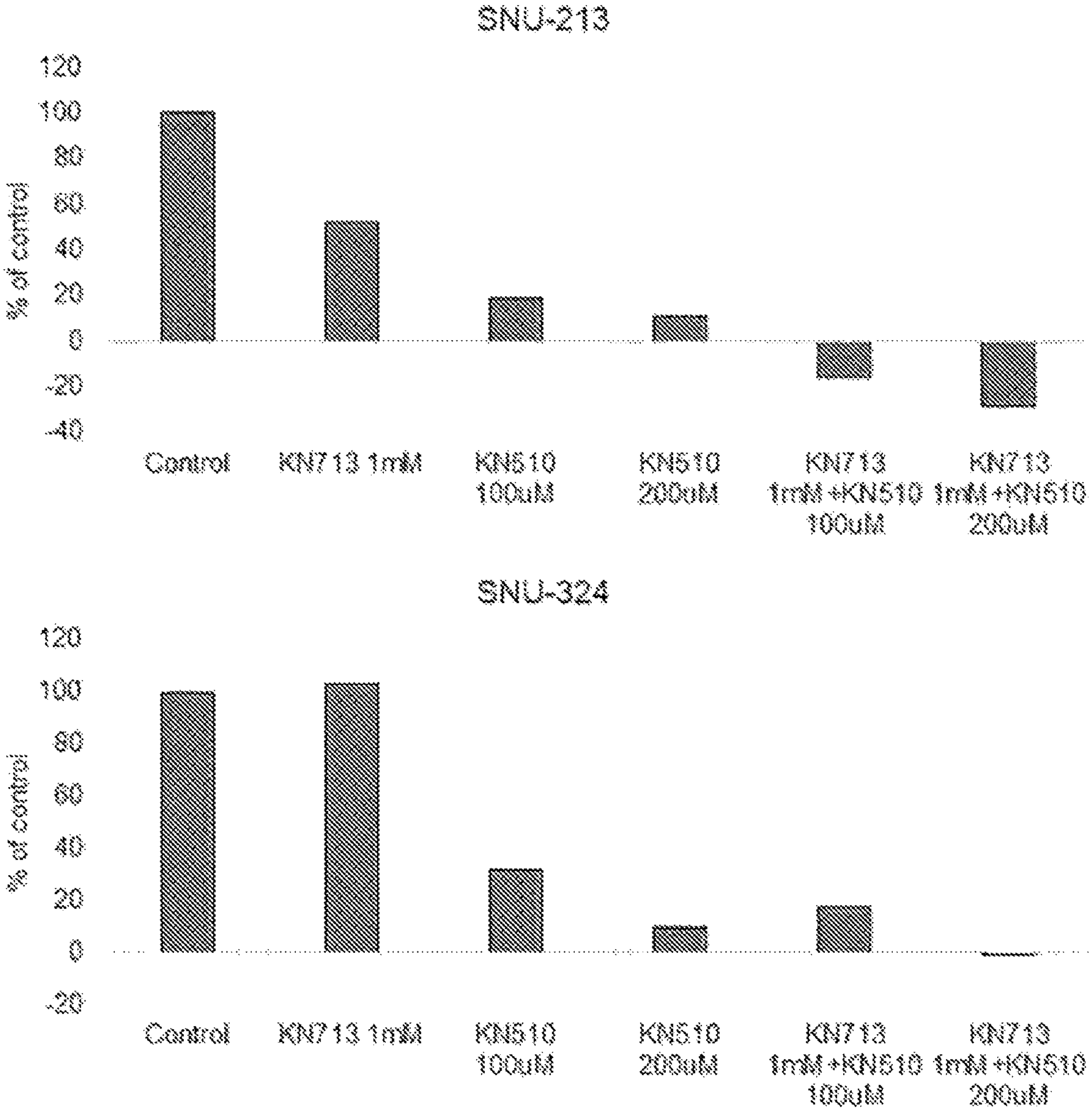
FIG. 3 shows the growth inhibitory effect of cell lines treated with trimetazidine (KN713) and/or omeprazole (KN510) on pancreatic cancer cell lines (SNU-213 and SNU-324). It was confirmed that the growth of the cell line was significantly inhibited when treated in combination with trimetazidine and omeprazole compared to the case where trimetazidine or omeprazole was treated alone.

As a result, as shown in [FIG. 1] to [FIG. 3], synergic effects occurred when trimetazidine and omeprazole were treated in combination compared to when treated alone, thereby the inhibitory effect of cancer cell line growth was significantly increased. The following [Table 1] to [Table 3] show the degree of growth inhibition (% compared to the control group) for the pancreatic cancer cell lines of [FIG. 1] to [FIG. 3], respectively.

TABLE 1

| | Mia PaCa2 | Capan1 |
|---|---|---|
| Control | 0 | 0 |
| KN713 1 mM | 30.24 | 31.20 |
| KN510 100 μM | 70.83 | 97.63 |
| KN510 200 μM | 92.75 | 111.22 |
| KN713 1 mM + KN510 100 μM | 73.06 | 125.91 |
| KN713 1 mM + KN510 200 μM | 161.62 | 156.95 |

TABLE 2

| | Capan2 | BX-PC3 |
|---|---|---|
| Control | 0 | 0 |
| KN713 1 mM | −22.25 | 12.30 |
| .KN510 100 μM | 1.30 | 79.47 |
| KN510 200 μM | 49.49 | 96.87 |

TABLE 2-continued

| | Capan2 | BX-PC3 |
|---|---|---|
| KN713 1 mM + KN510 100 μM | 53.83 | 108.81 |
| KN713 1 mM + KN510 200 μM | 111.23 | 131.07 |

TABLE 3

| | SNU-213 | SNU-324 |
|---|---|---|
| Control | 0 | 0 |
| KN713 1 mM | 48.13 | −3.16 |
| KN510 100 μM | 80.98 | 68.23 |
| KN510 200 μM | 89.59 | 89.81 |
| KN713 1 mM + KN510 100 μM | 115.85 | 82.30 |
| KN713 1 mM + KN510 200 μM | 128.65 | 100.74 |

Example 2

Oxygen Consumption Measurement

OCR (oxygen consumption rate), basal respiration and ATP production (ATP) in the presence of linoleic acid-BSA, oleic acid-BSA or BSA using XF96 Extracellular Flux Analyzer (Seahorse Bioscience, North Billerica, MA, USA) Production) was measured.

Specifically, cells were plated on MIA PaCa-2 cell culture plates (Seahorse Bioscience, North Billerica). MIA PaCa-2 cells were each seeded at 15,000 cells/well (XF96 plate), and cultured for 24 hours in a humidified 37° C. incubator of 5% $CO_2$. Prior to performing the assay, the growth medium in the wells had a minimum concentration of 1:1000, and 170 μl of the assay medium was added to the cells. While calibrating the sensor cartridge, the cell plate was incubated for 60 min in a 37° C./non-$CO_2$ incubator prior to the start of the assay. All experiments were performed at 37° C. Each measurement cycle consisted of a mixing time of 2 min and a data collection cycle time of 4 min. Respiratory chain inhibitor of oligomycin, FCCP (carbonyl cyanide-4-(trifluoromethoxy)phenylhydrazone), Rotenone & antymycin A were prepared in an appropriate concentration in the cartridge, adjusted to pH 7.4, and added to each injection port. Three baselines were measured before addition of the respiratory chain inhibitor, and three responses were measured after each addition. The OCR data points represent the average absolute velocity (moles/min) over the measurement period. [Table 4] shows the basal respiratory volume to ATP production in [FIG. 4].

TABLE 4

| | Basal Respiration | ATP Production |
|---|---|---|
| Control | 91.55 | 77.12 |
| KN713 1 mM | 81.59 | 68.33 |
| KN510 200 μM | 45.59 | 36.88 |
| KN713 1 mM + KN510 200 μM | 17.46 | 13.57 |

Figure 4:
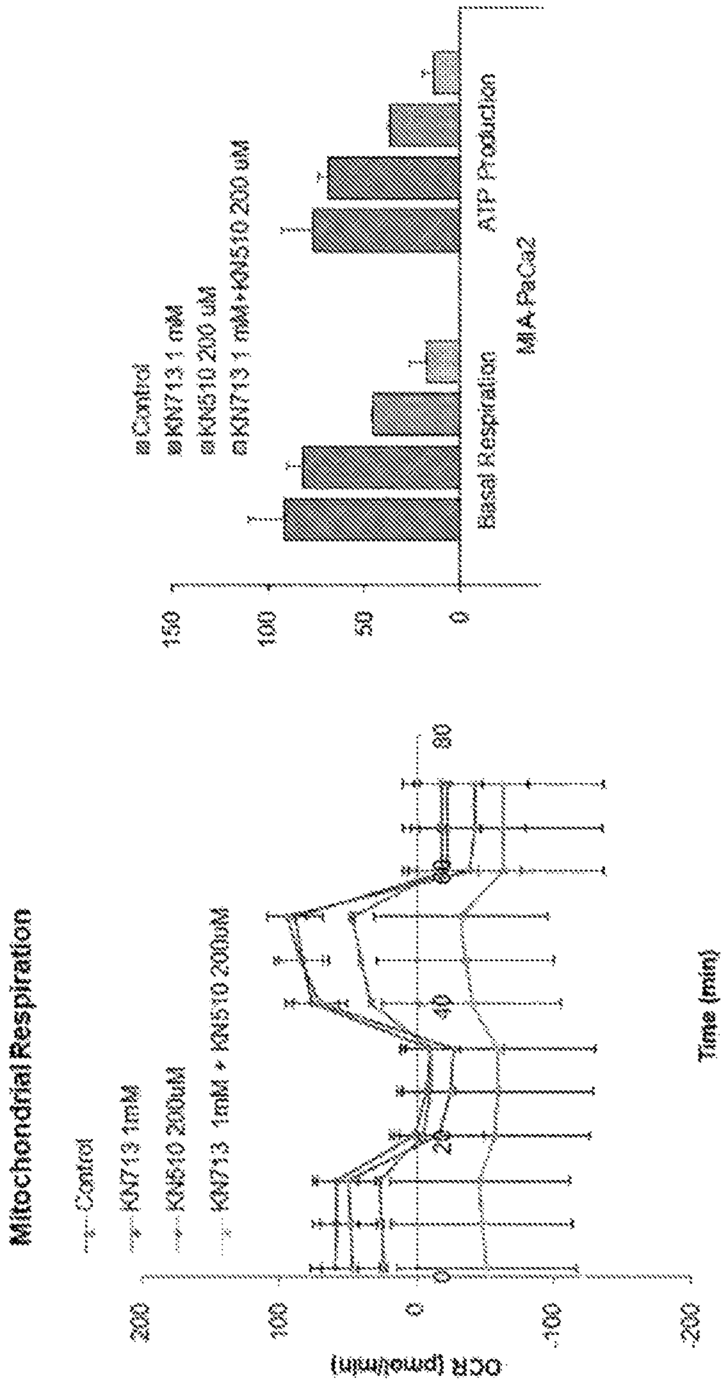
FIG. 4 shows the oxygen consumption of the pancreatic cancer cell line MIA PaCa2 treated with trimetazidine (KN713) and/or omeprazole (KN510). It was confirmed that the oxygen consumption was significantly reduced when treated in combination with trimetazidine and omeprazole compared to the case where trimetazidine or omeprazole was treated alone.

As a result, as shown in [FIG. 4], it was confirmed that oxygen consumption, basal respiration, and ATP production were significantly reduced when trimetazidine and omeprazole were treated in combination compared to when treated alone.

Example 3

Xenograft Tumor Model

MIA PaCa-2 cells (1×10 7) in 100 μl PBS were subcutaneously inoculated into 6-8 weeks old Balb/c-nu mice (Orient, Seoul, Korea) using a 1 ml syringe. After one week, the mice were divided into three groups: a control group (solvent treatment), a KN713 40 mg/kg/100 μl treatment group, and a KN713 80 mg/kg/200 μl treatment group. KN713 was administered intraperitoneally once a day (for 49 days, 6 days/week, n=7). The primary tumor size was measured weekly using a caliper, and the tumor volume was calculated using the formula $V=(A\times B^2)/2$ (V=volume ($mm^3$), A=long diameter, B=short diameter). This experiment was reviewed and approved by the Institutional Animal Care and Use Committee (IACUC) of the National Cancer Center Research Institute, which was established by the International Association for Accreditation of Laboratory Animals (It was accredited by AAALAC International). [Table 5] shows the tumor size of [FIG. 5].

TABLE 5

| | 3 | 4 | 5 | 6 | 7 | 8 |
|---|---|---|---|---|---|---|
| Control | 148.59 | 448.52 | 748.89 | 944.41 | 1472.13 | 1709.54 |
| 40 mg/kg | 147.09 | 319.40 | 499.29 | 593.57 | 790.38 | 965.18 |
| 80 mg/kg | 147.36 | 279.36 | 372.00 | 420.82 | 589.49 | 555.42 |

Figure 5:
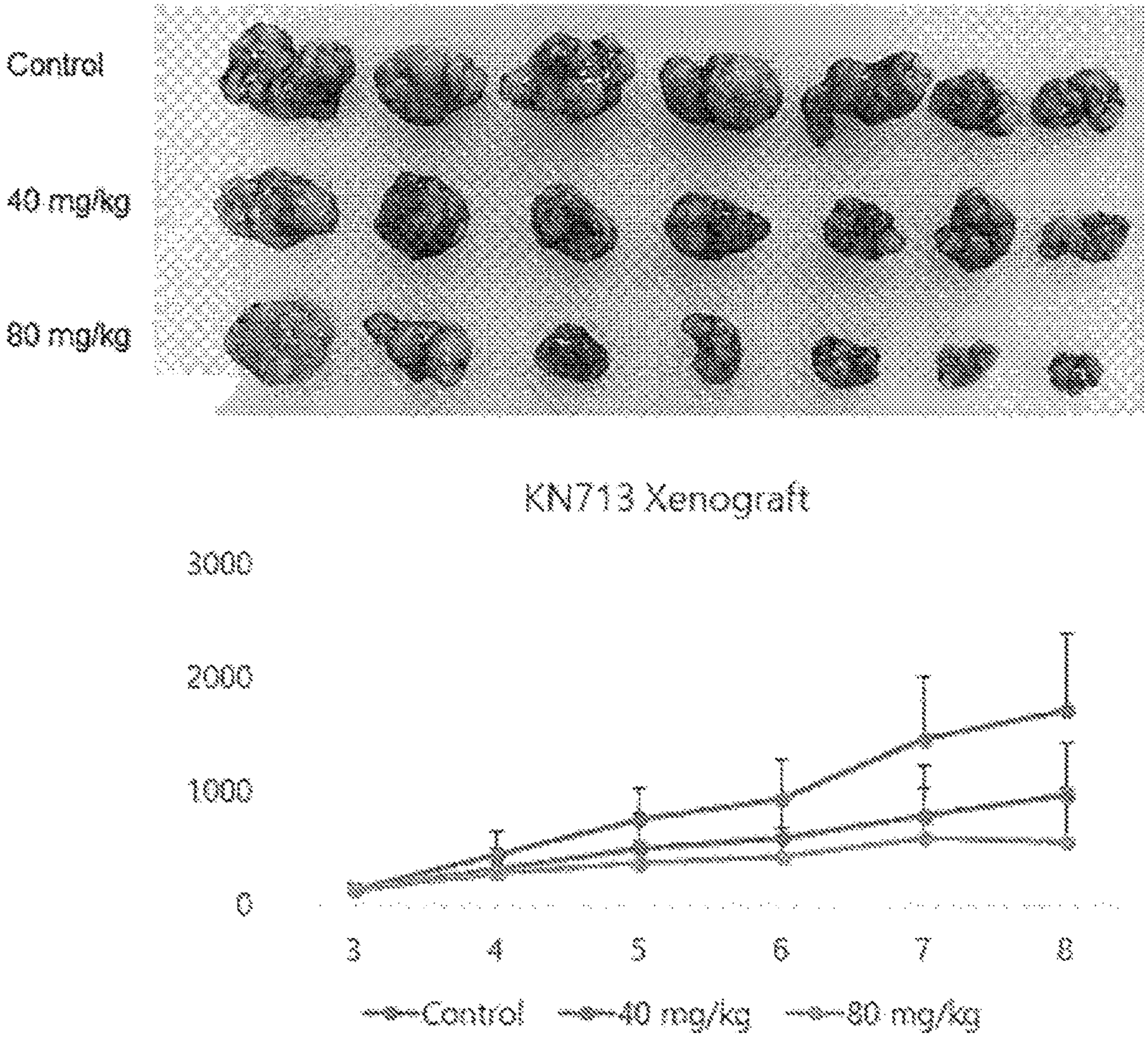
FIG. 5 shows a change in tumor size according to administration of trimetazidine (KN713) to a mouse model transplanted with the pancreatic cancer cell line MIA PaCa2. As the dose of KN713 increased, it was confirmed that the tumor size was significantly suppressed.
Figure 6:
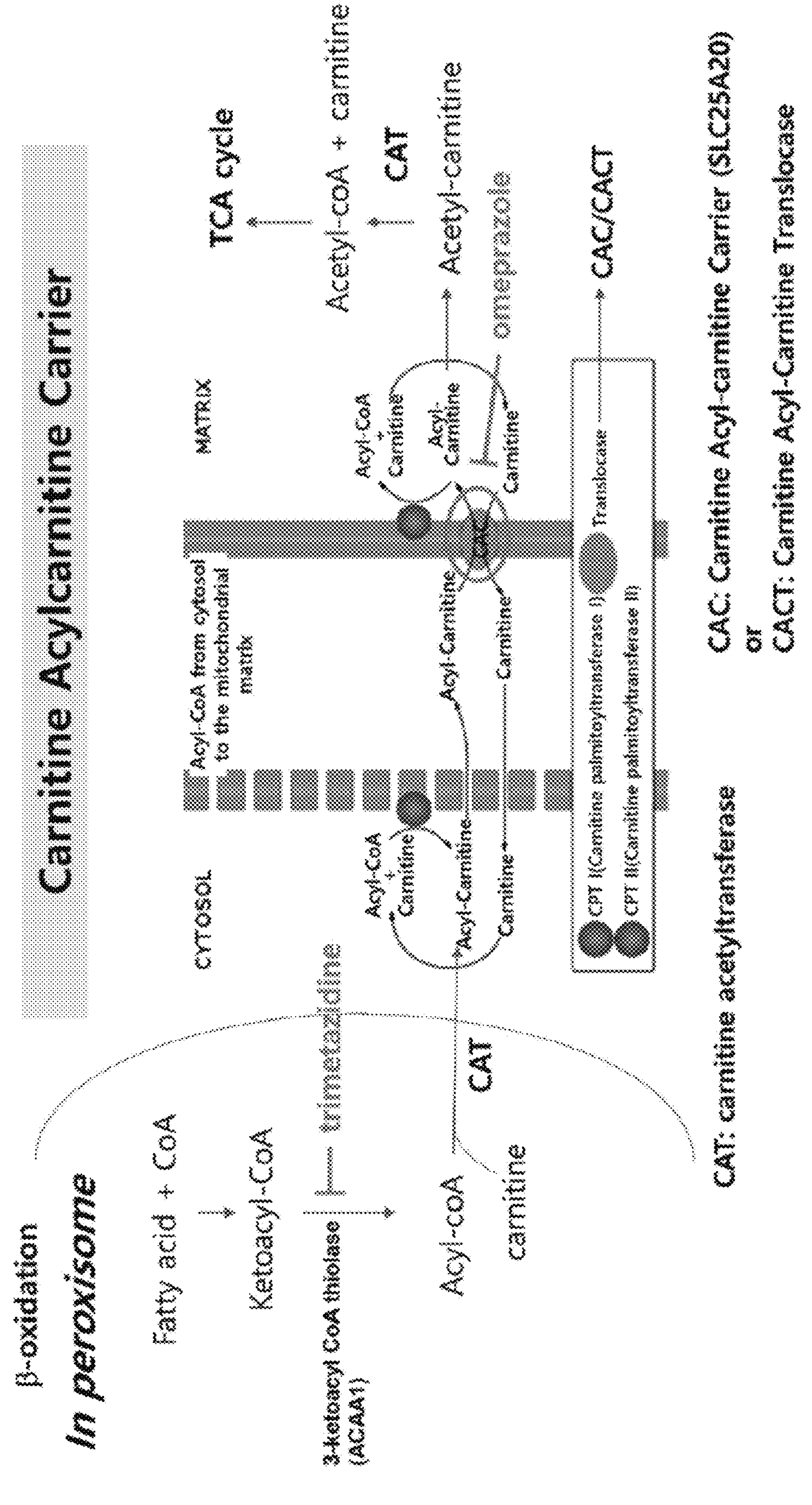
FIG. 6 shows the action points of trimetazidine and omeprazole. Trimetazidine inhibits 3-ketoacyl CoA thiolase (ACAA) in the peroxisome, and omeprazole inhibits carnitine acylcarnitine carrier transport in the mitochondria.

As a result, as shown in [FIG. 5], it was confirmed that the size of the tumor was significantly reduced when treated in combination with trimetazidine and omeprazole compared to when treated alone.

Example 4

SRB Analysis 2

Through SRB analysis, the effect of the combined treatment of a CAC inhibitor and an ACAA inhibitor on cell growth in the pancreatic cancer cells SW1990, MIA PaCa2, Panc-1, SU.86.86, BxPC-3, AsPC-1, SNU-213, SNU-324 was analyzed. The degree of cell growth based on the control (100%) was analyzed.

The SRB assay was performed as follows: each cell line (100 μl) was seeded into 96-well microtiter plates at densities ranging from 5,000 to 20,000 cells/well depending on the doubling time of each cell line. After cell seeding, microtiter plates were incubated for 24 h before addition of experimental drug. Drugs were prepared at the indicated concentrations and 100 μl was added to each well; The plates were then incubated in a $CO_2$ incubator. Then, cold TCA was added to terminate the assay. Cells were fixed in situ by gentle addition of 50 μl of cold 50% (w/v) TCA (final concentration: 10% TCA) and incubated at 4° C. for 60 min. The supernatant was discarded and the plate was washed 5 times with tap water and then air dried. A solution (100 μl) of 0.4% (w/v) SRB (Sulforhodamine B) in 1% acetic acid was added to each well, and the plate was left at room temperature for 10 minutes. After staining, the plates were air dried after washing 5 times with 1% acetic acid to remove unbound dye. The bound dye was then solubilized with 10 mM trizma base and the absorbance was recorded at 515 nm using an automated plate reader.

Figure 7A:
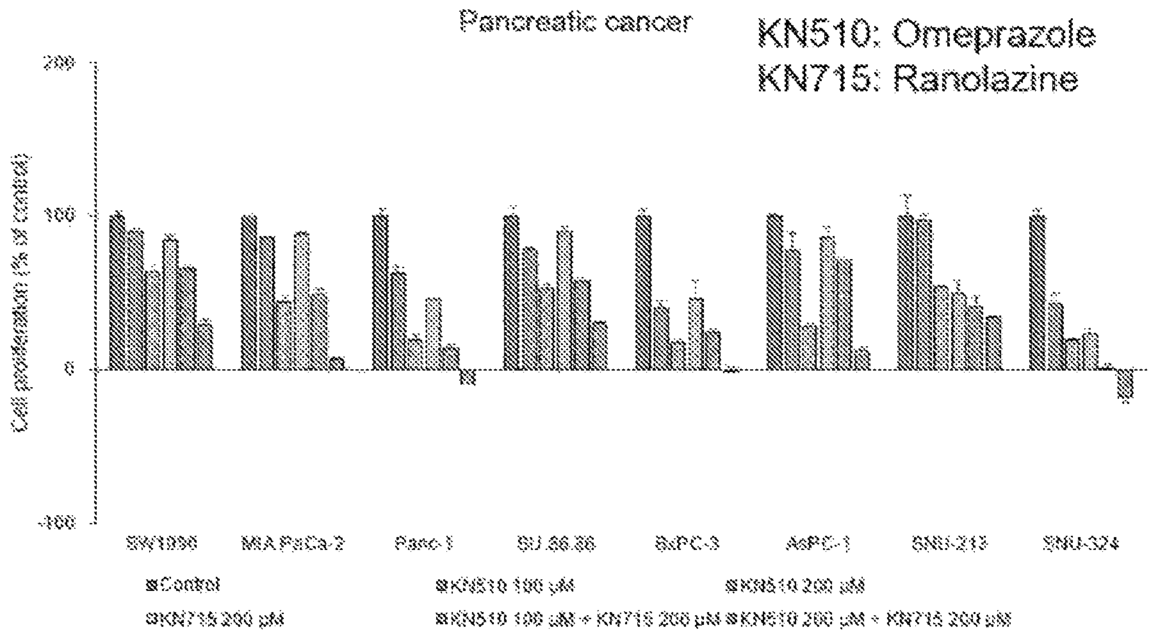
FIG. 7*a* shows the results of analyzing the effect of the combined treatment of the CAC inhibitor KN510 (Omeprazole) and the ACAA inhibitor KN715 (Ranolazine).

FIG. 7*a* and Table 6 show the results of analyzing the effect of the combined treatment of the CAC inhibitor KN510 (Omeprazole) and the ACAA inhibitor KN715 (Ranolazine). This is the result of treatment with Control, KN510 100 μM alone, KN510 200 μM alone, KN715 200 μM alone, KN510 100 μM+KN715 200 μM (combination treatment), KN510 200 μM+KN715 200 μM (combination treatment) in pancreatic cancer cell lines for 48 hours. As shown in FIG. 7*a* and Table 6, when the CAC inhibitor KN510 (Omeprazole) and the ACAA inhibitor KN715 (Ranolazine) were co-treated, it was confirmed that cell growth was significantly inhibited.

TABLE 6

| | | | | | | | | |
|---|---|---|---|---|---|---|---|---|
| Control | 100.00 | 100.00 | 100.00 | 100.00 | 100.00 | 100.00 | 100.00 | 100.00 |
| KN510 100 μM | 90.16 | 86.46 | 63.06 | 78.12 | 40.19 | 77.31 | 97.11 | 43.26 |
| KN510 200 μM | 63.83 | 44.41 | 19.45 | 53.01 | 17.37 | 28.00 | 54.29 | 19.68 |
| KN715 200 μM | 84.42 | 87.91 | 45.56 | 90.37 | 46.24 | 86.53 | 50.00 | 23.58 |
| KN510 100 μM + KN715 200 μM | 66.15 | 48.61 | 13.74 | 58.10 | 24.05 | 71.08 | 40.67 | 0.37 |
| KN510 200 μM + KN715 200 μM | 28.98 | 6.73 | −8.57 | 30.76 | −0.57 | 12.68 | 33.86 | −17.58 |

Figure 7B:
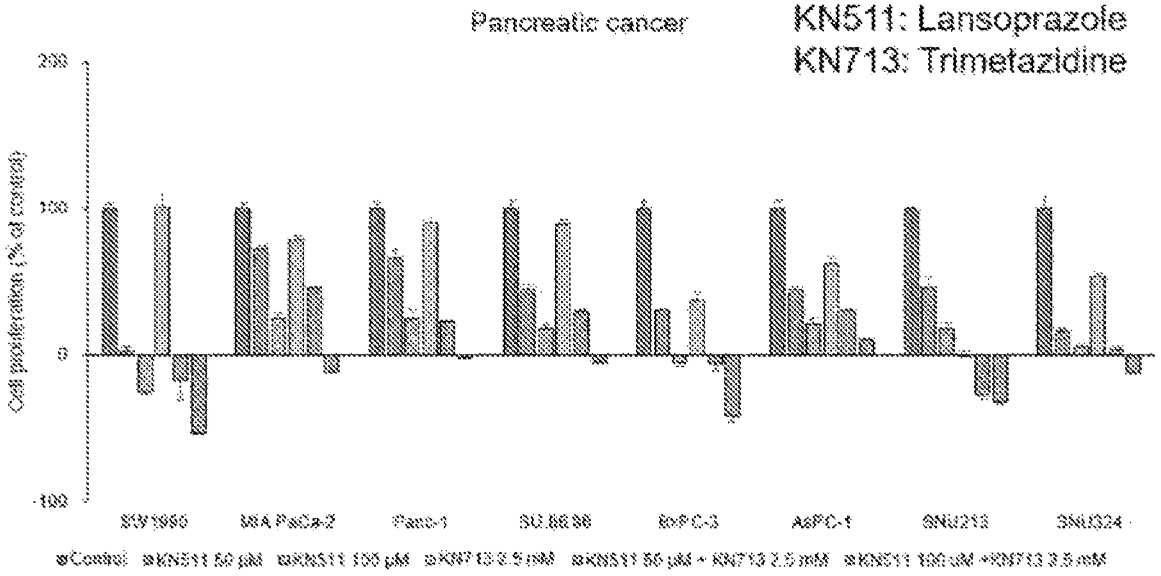
FIG. 7*b* shows the results of analyzing the effect of the combined treatment of the CAC inhibitor KN511 (Lansoprazole) and the ACAA inhibitor KN713 (Trimetazidine).

FIG. 7*b* and Table 7 show the results of analyzing the effect of the combined treatment of the CAC inhibitor KN511 (Lansoprazole) and the ACAA inhibitor KN713 (Trimetazidine). This is the result of treatment with Control, KN511 50 μM alone, KN511 100 μM alone, KN713 2.5 mM alone, KN511 50 μM+KN713 2.5 mM (combination treatment), KN511 100 μM+KN713 2.5 mM (combination treatment) in pancreatic cancer cell lines for 48 hours. As shown in FIG. 7*b* and Table 7, it was confirmed that cell growth was significantly inhibited when the CAC inhibitor KN511 (Lansoprazole) and the ACAA inhibitor KN713 (Trimetazidine) were co-treated.

TABLE 7

| | SW1990 | MIA PaCa-2 | Panc-1 | SU.86.86 | BxPC-3 | AsPC-1 | SNU213 | SNU324 |
|---|---|---|---|---|---|---|---|---|
| Control | 100.00 | 100.00 | 100.00 | 100.00 | 100.00 | 100.00 | 100.00 | 100.00 |
| KN511 50 μM | 2.62 | 72.22 | 65.77 | 44.93 | 30.51 | 44.46 | 46.12 | 16.15 |
| KN511 100 μM | −25.25 | 24.61 | 24.53 | 17.55 | −4.87 | 20.33 | 18.10 | 4.93 |
| KN713 2.5 mM | 100.37 | 78.16 | 90.36 | 88.97 | 36.83 | 61.66 | −0.24 | 53.40 |
| KN511 50 μM + KN713 2.5 mM | −17.47 | 45.45 | 22.57 | 29.28 | -5.87 | 30.22 | −27.75 | 3.95 |
| KN511 100 μM + KN713 2.5 mM | −52.78 | −11.98 | −2.61 | −4.91 | −41.27 | 10.21 | −31.83 | −11.52 |

Figure 7C:
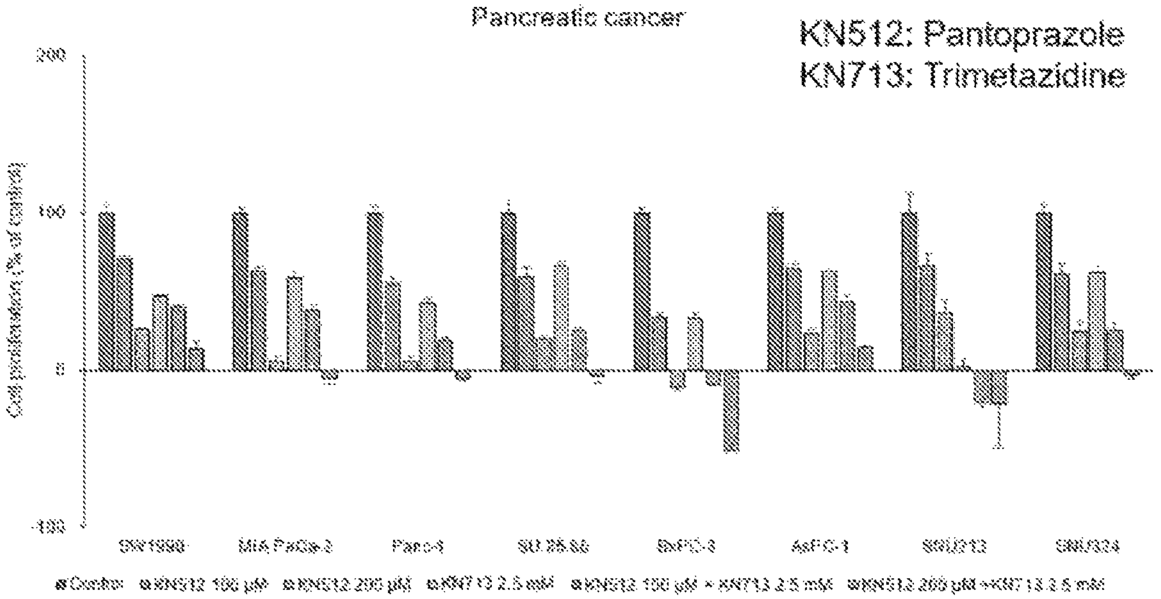
FIG. 7*c* shows the results of analyzing the effect of the combined treatment of the CAC inhibitor KN512 (Pantoprazole) and the ACAA inhibitor KN713 (Trimetazidine).

FIG. 7*c* and Table 8 show the results of analyzing the effect of the combined treatment of the CAC inhibitor KN512 (Pantoprazole) and the ACAA inhibitor KN713 (Trimetazidine). This is the result of treatment with Control, KN512 100 μM alone, KN512 200 μM alone, KN713 2.5 mM alone, KN511 50 μM+KN713 2.5 mM (combination treatment), KN512 100 μM+KN713 2.5 mM (combination treatment) in pancreatic cancer cell lines for 48 hours. As shown in FIG. 7*c* and Table 8, when the CAC inhibitor KN512 (Pantoprazole) and the ACAA inhibitor KN713 (Trimetazidine) were co-treated, cell growth was significantly inhibited.

TABLE 8

| | MIA PaCa-2 | Panc-1 | SW1990 | SU.86.86 | SNU213 | SNU324 | AsPC-1 | BxPC-3 |
|---|---|---|---|---|---|---|---|---|
| Control | 100.00 | 100.00 | 100.00 | 100.00 | 100.00 | 100.00 | 100.00 | 100.00 |
| KN512 100 μM | 62.60 | 54.90 | 70.30 | 59.26 | 66.09 | 61.20 | 64.75 | 34.14 |
| KN512 200 μM | 5.82 | 6.03 | 25.58 | 19.69 | 36.60 | 23.82 | 23.37 | −10.63 |
| KN713 2.5 mM | 58.31 | 42.98 | 47.15 | 65.95 | 1.98 | 61.55 | 62.56 | 32.97 |
| KN512 100 μM + KN713 2.5 mM | 37.92 | 18.55 | 39.85 | 24.79 | −20.29 | 24.62 | 43.78 | −9.31 |
| KN512 200 μM + KN713 2.5 mM | −5.90 | −5.66 | 13.95 | −3.96 | −21.51 | −3.03 | 14.15 | −51.24 |

Figure 7D:
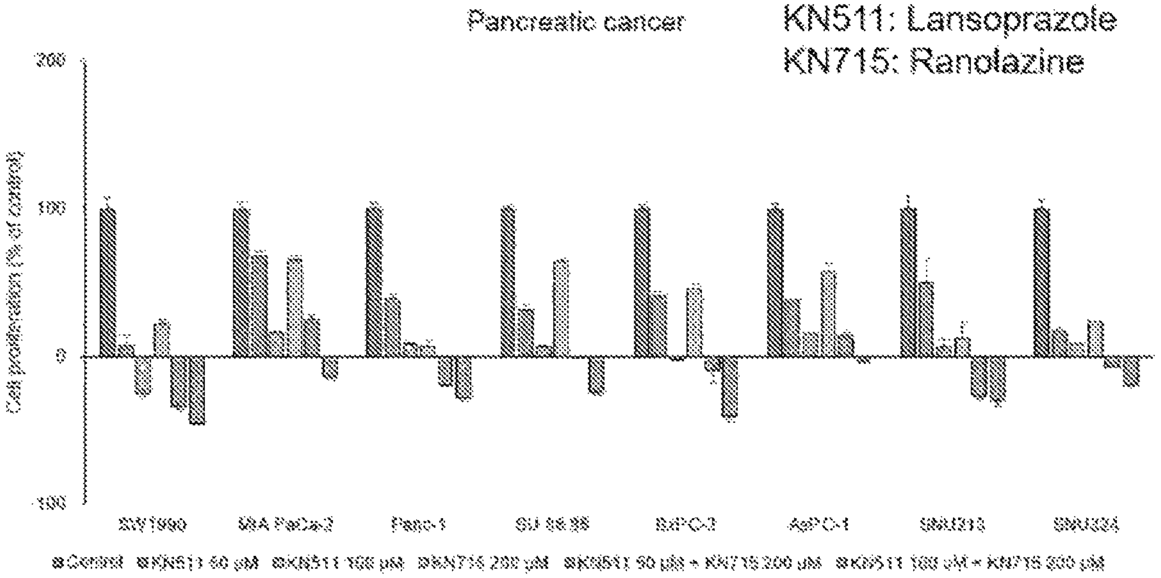
FIG. 7*d* shows the results of analyzing the effect of the combined treatment of the CAC inhibitor KN511 (Lansoprazole) and the ACAA inhibitor KN715 (Ranolazine).
Figure 8A:
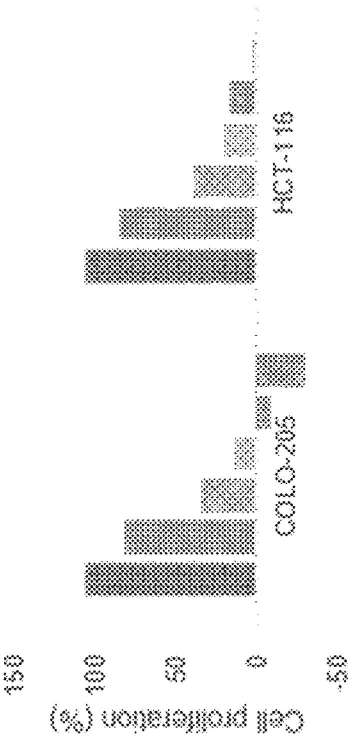
FIGS. 8*a* and 8*b* show the results of the analysis the effect of triple combination treatment of CAC inhibitor (KN510: omeprazole), ACAA inhibitor (KN713: trimetazidine) and anticancer drug on cell growth in a colon cancer cell line.
Figure 8A:
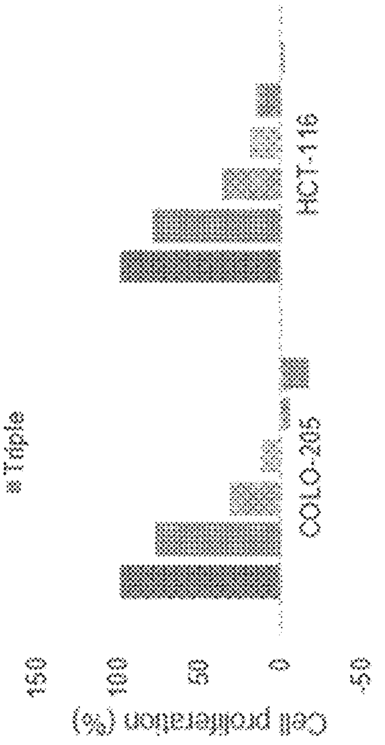
Figure 8B:
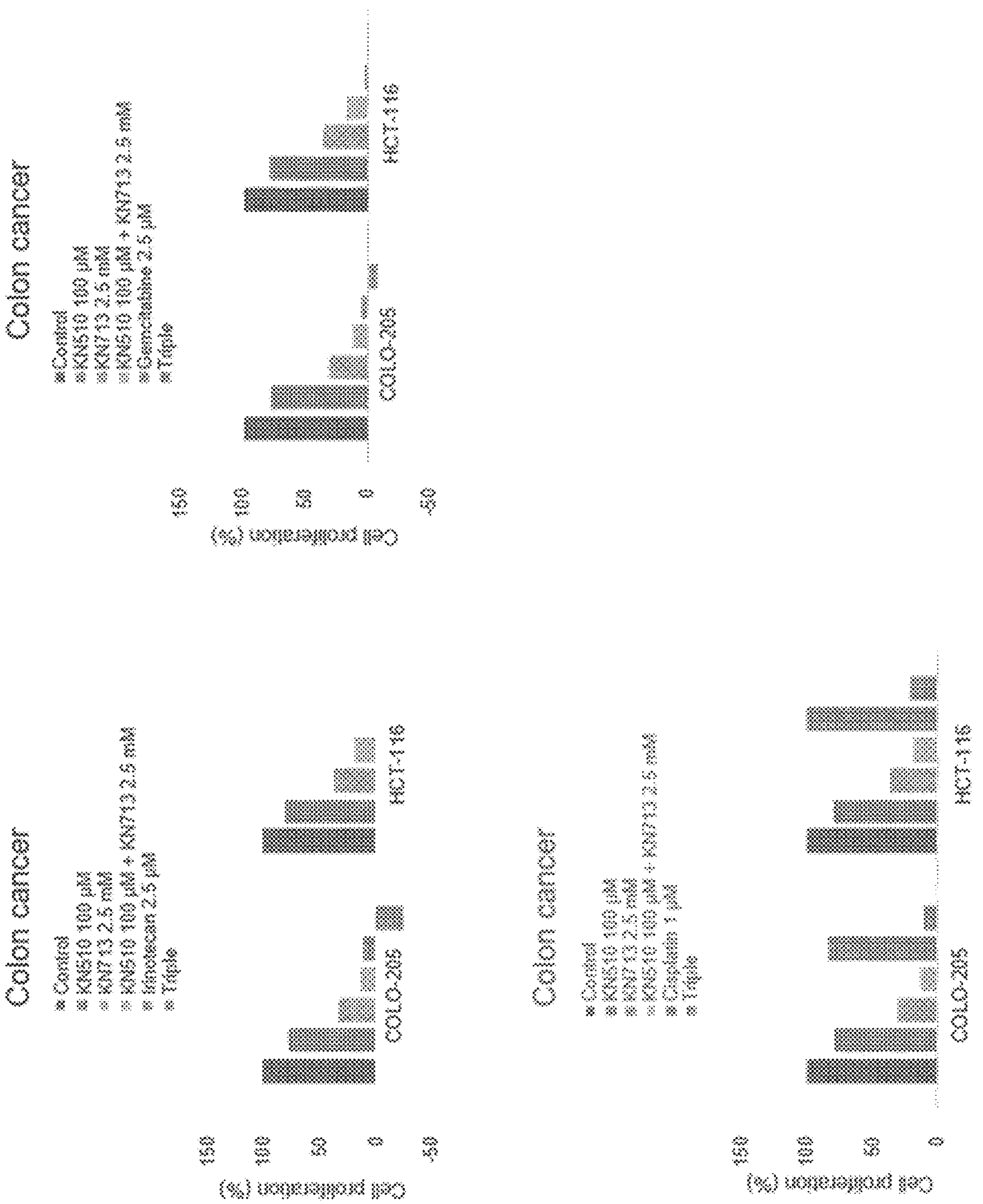
Figure 9A:
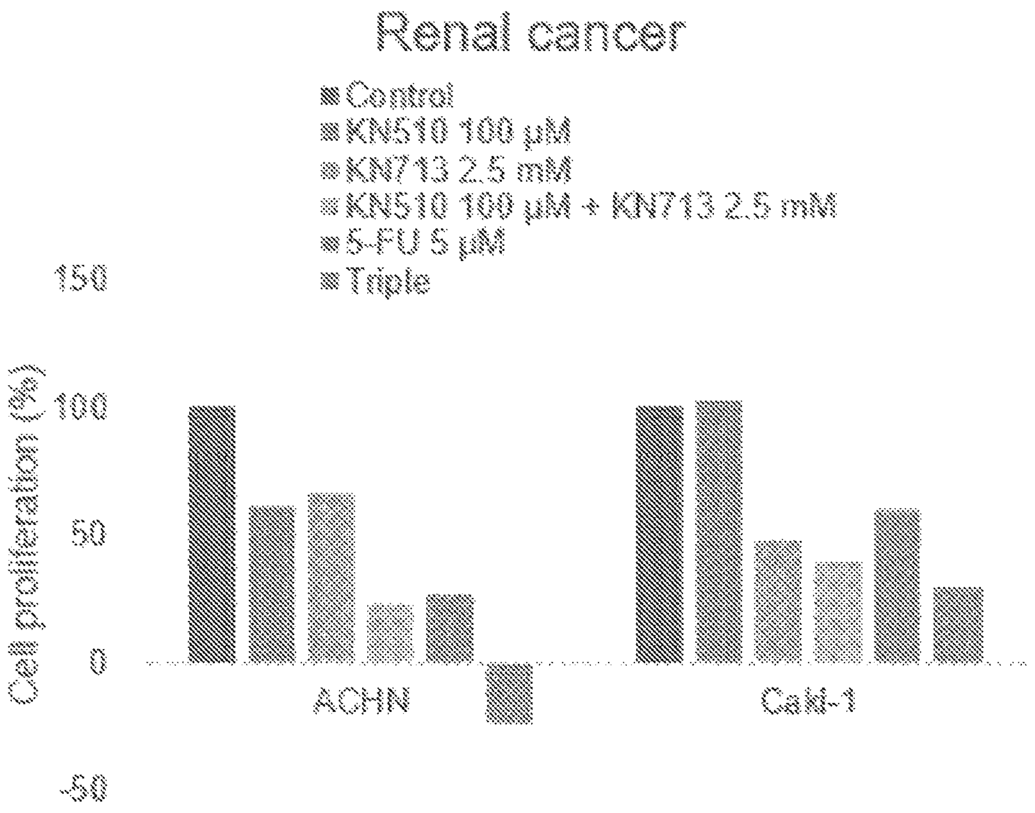
FIGS. 9*a* and 9*b* show the results of the analysis the effect of triple combination treatment of CAC inhibitor (KN510: omeprazole), ACAA inhibitor (KN713: trimetazidine) and anticancer drug on cell growth in a renal cancer cell line.
Figure 9B:
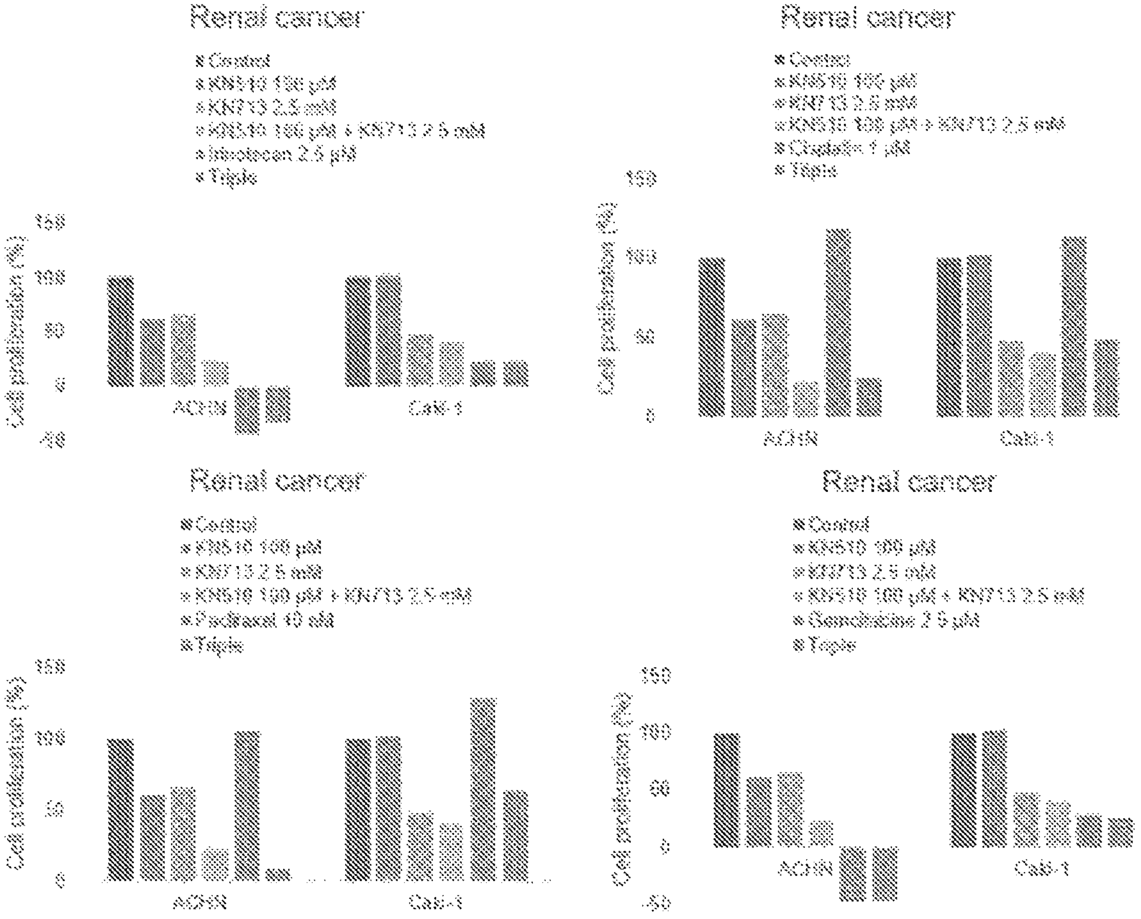
Figure 10A:
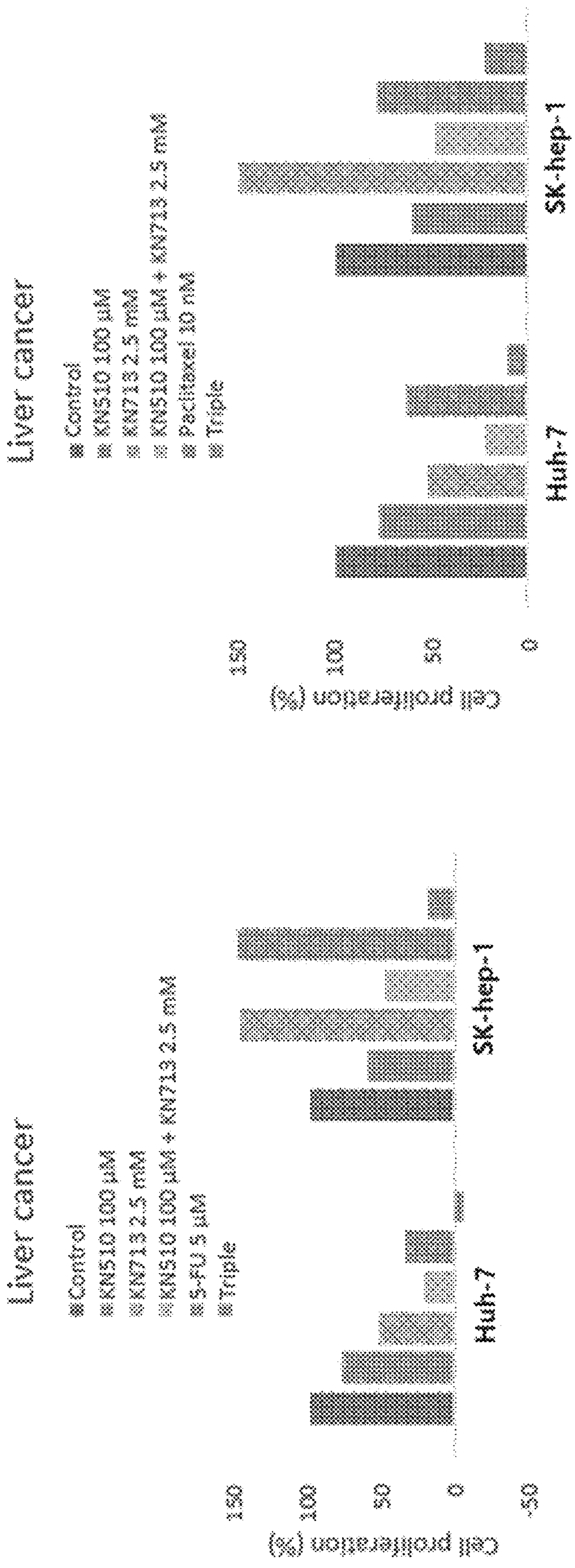
FIGS. 10*a* and 10*b* show the results of the analysis the effect of triple combination treatment of CAC inhibitor (KN510: omeprazole), ACAA inhibitor (KN713: trimetazidine) and anticancer drug on cell growth in a liver cancer cell line.
Figure 10B:
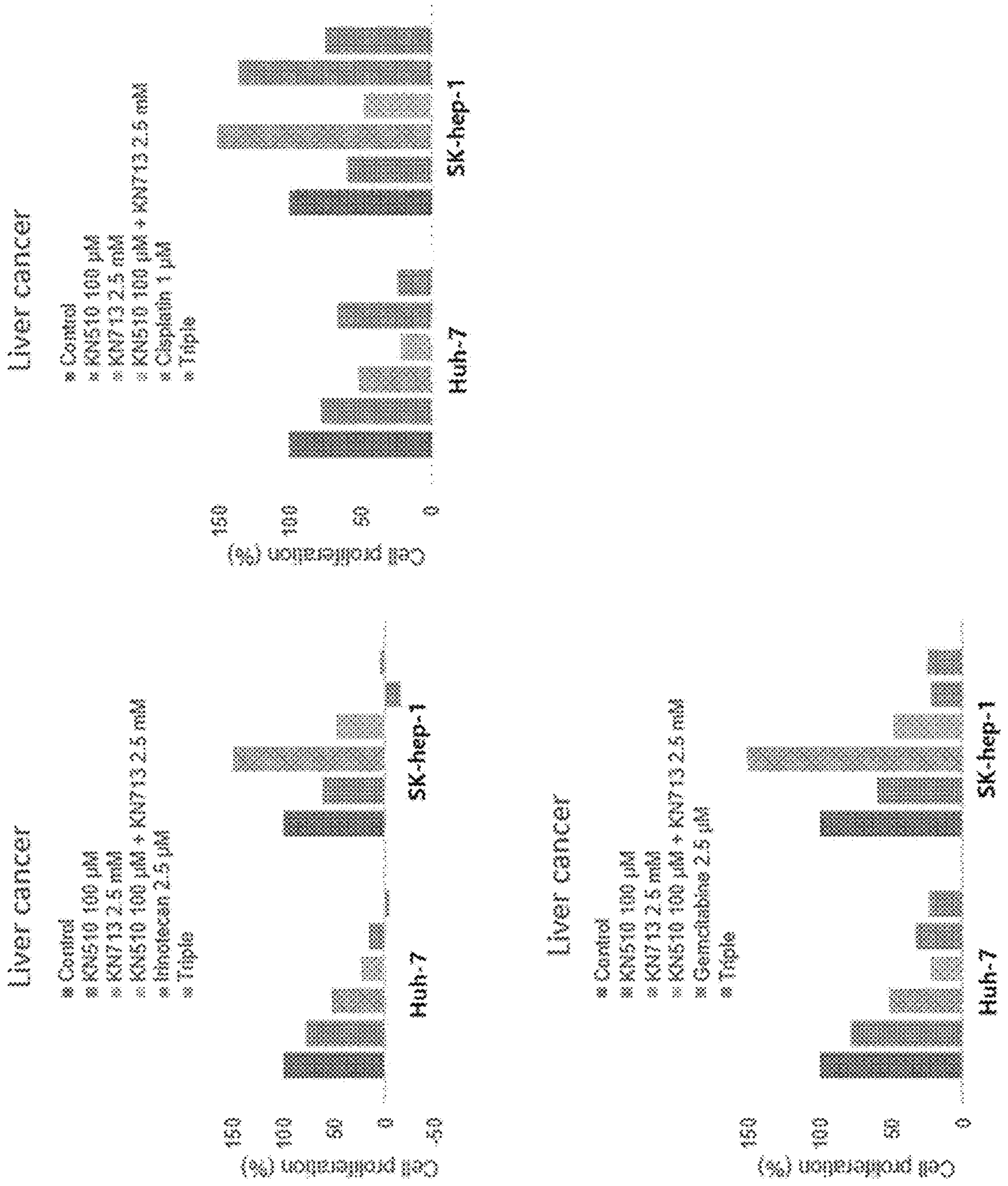
Figure 11A:
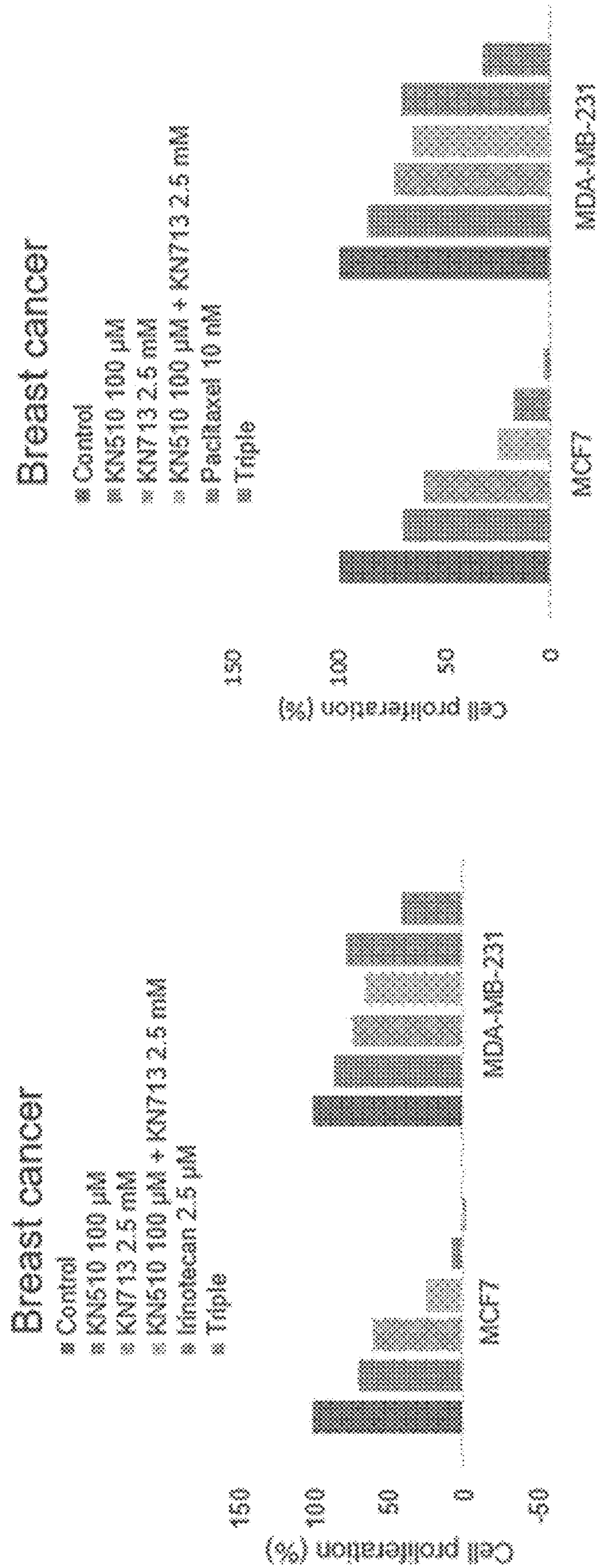
FIGS. 11*a* and 11*b* show the results of the analysis the effect of triple combination treatment of CAC inhibitor (KN510: omeprazole), ACAA inhibitor (KN713: trimetazidine) and anticancer drug on cell growth in a breast cancer cell line.
Figure 11B:
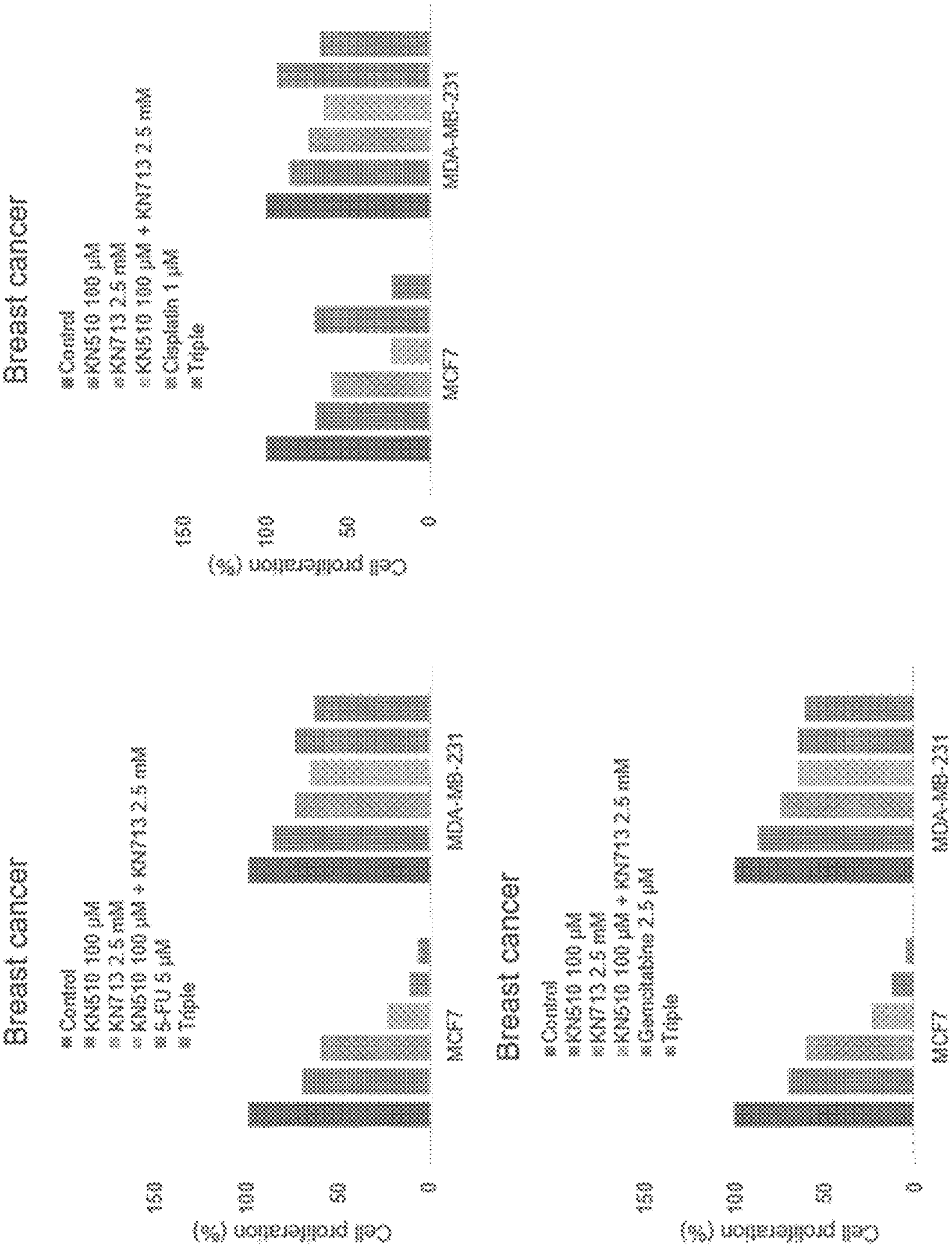
Figure 12A:
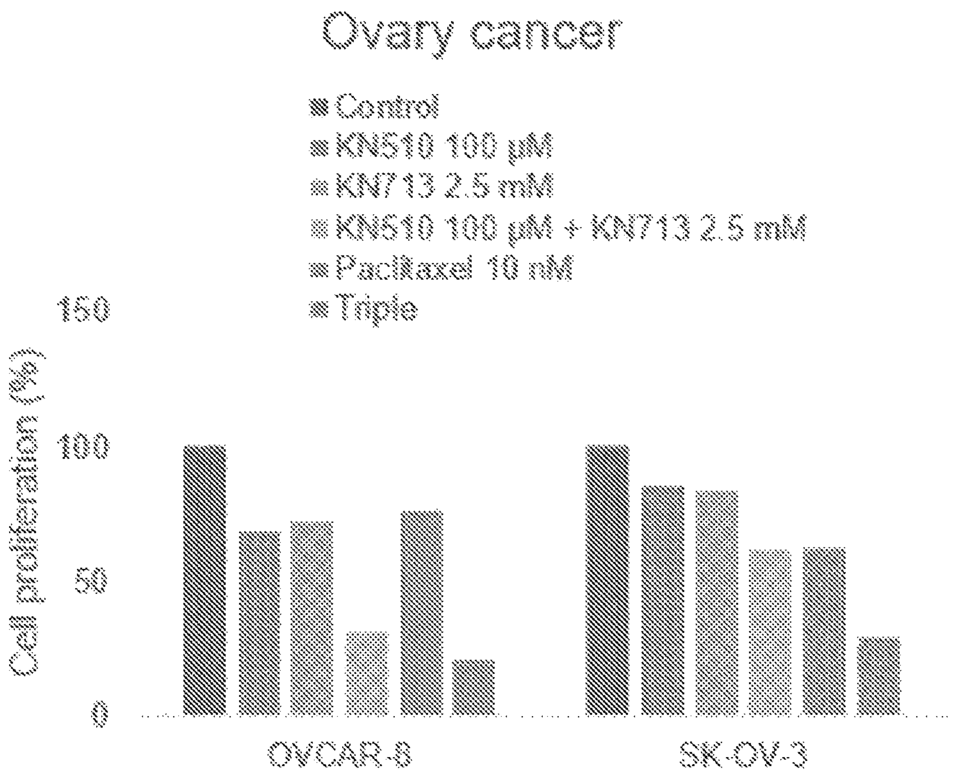
FIGS. 12*a* and 12*b* show the results of the analysis the effect of triple combination treatment of CAC inhibitor (KN510: omeprazole), ACAA inhibitor (KN713: trimetazidine) and anticancer drug on cell growth in an ovarian cancer cell line.
Figure 12B:
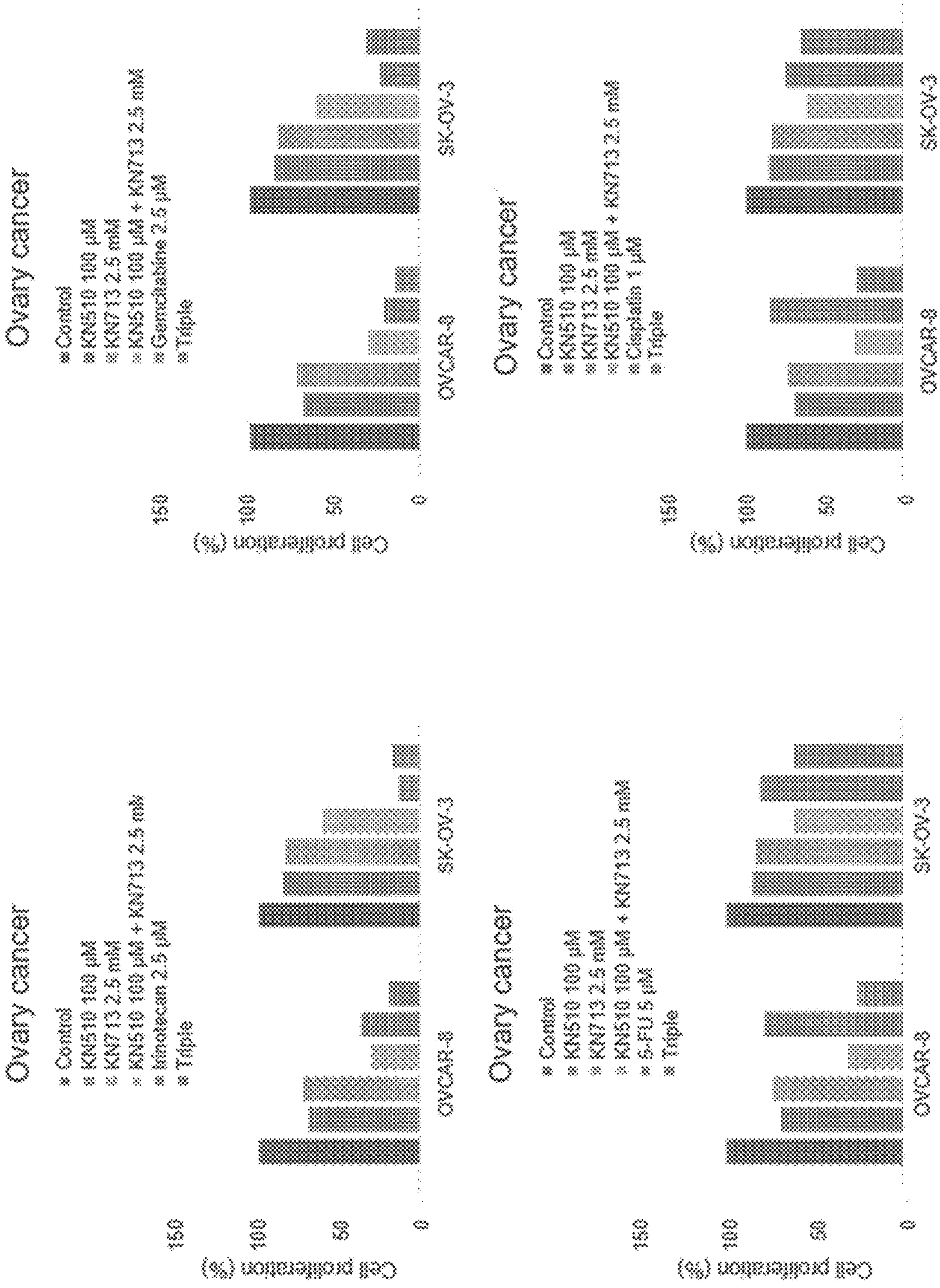
Figure 13A:
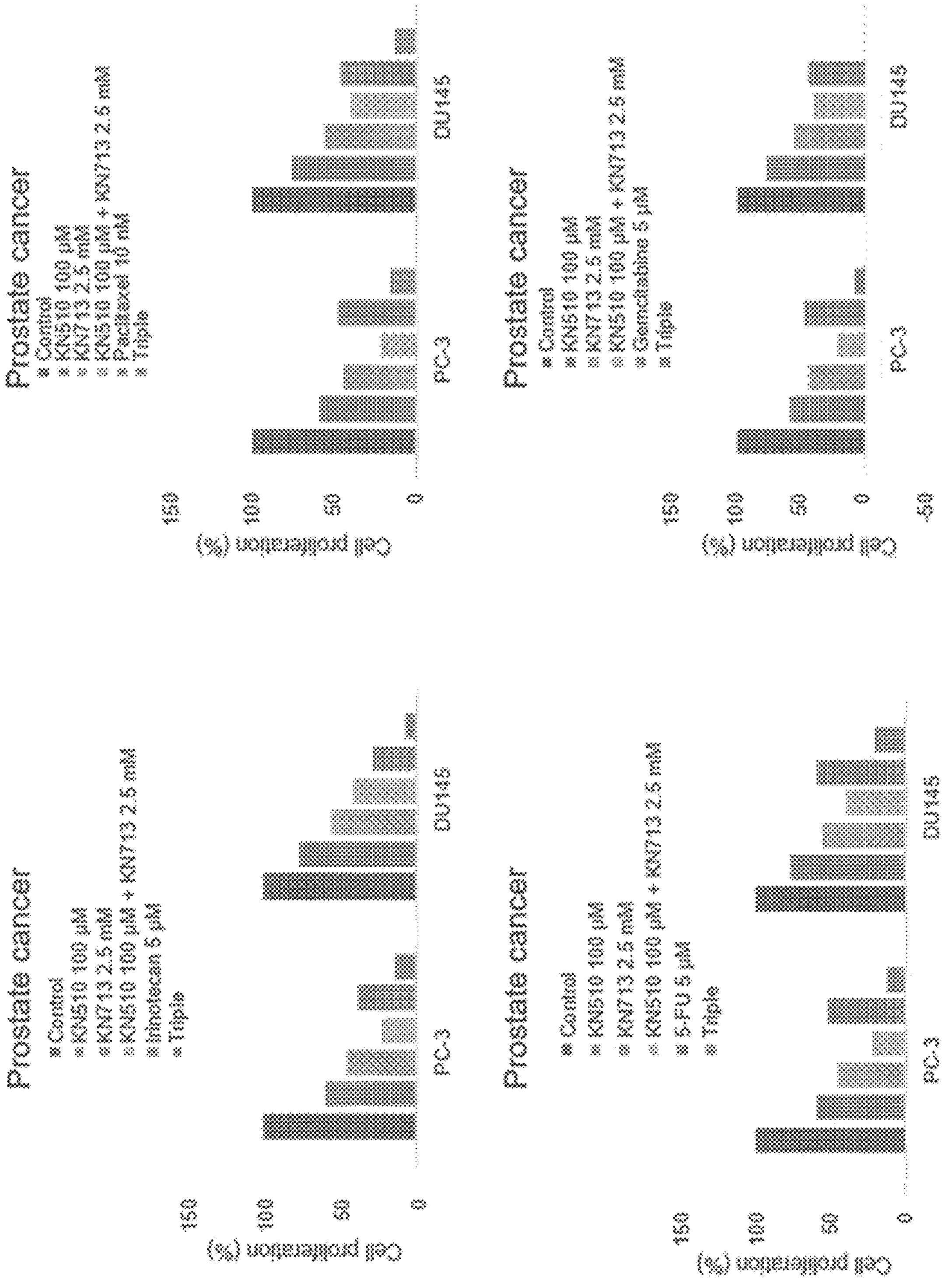
FIGS. 13*a* and 13*b* show the results of the analysis the effect of triple combination treatment of CAC inhibitor (KN510: omeprazole), ACAA inhibitor (KN713: trimetazidine) and anticancer drug on cell growth in a prostate cancer cell line.
Figure 13B:
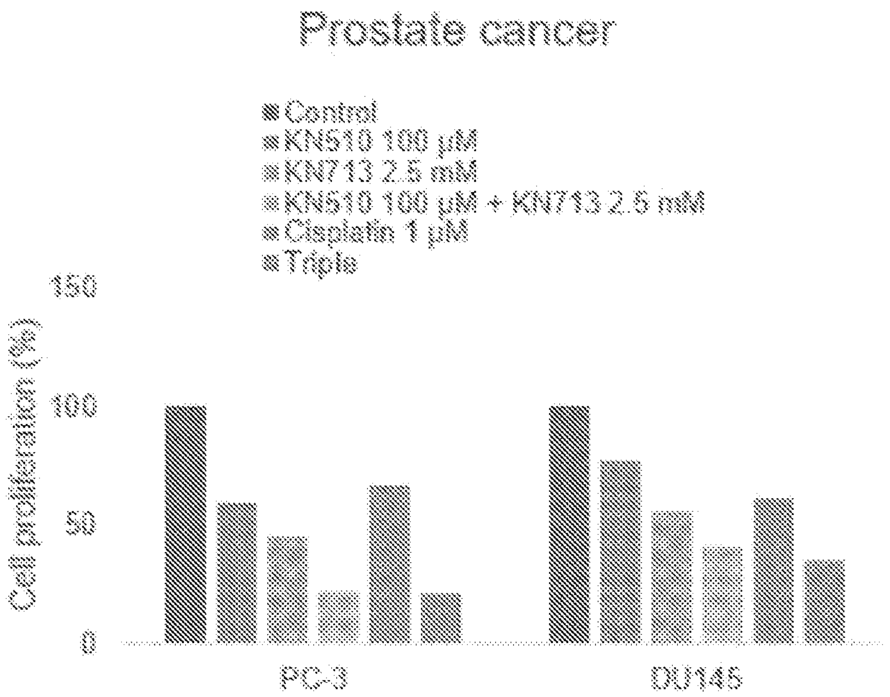
Figure 14A:
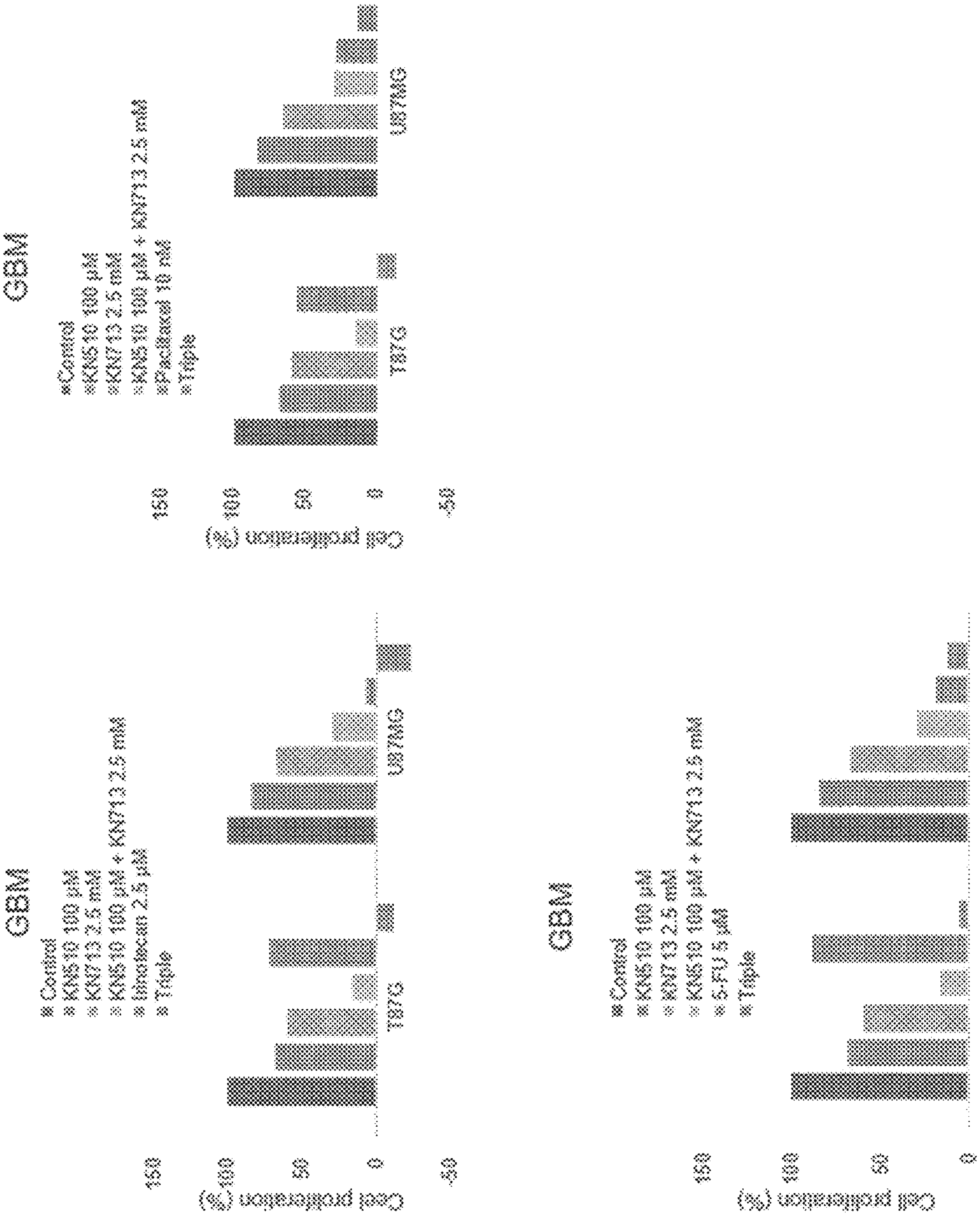
FIGS. 14*a* and 14*b* show the results of the analysis the effect of triple combination treatment of CAC inhibitor (KN510: omeprazole), ACAA inhibitor (KN713: trimetazidine) and anticancer drug on cell growth in a glioblastoma (GBM) cell line.
Figure 14B:
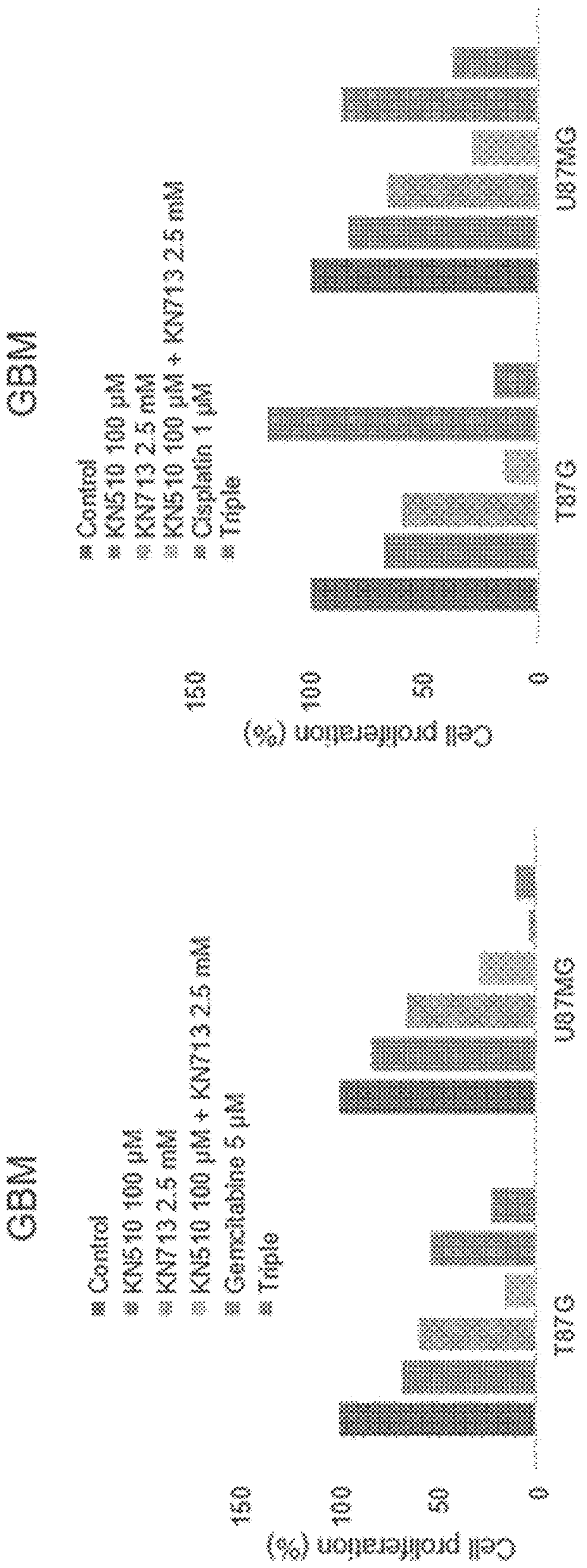
Figure 15A:
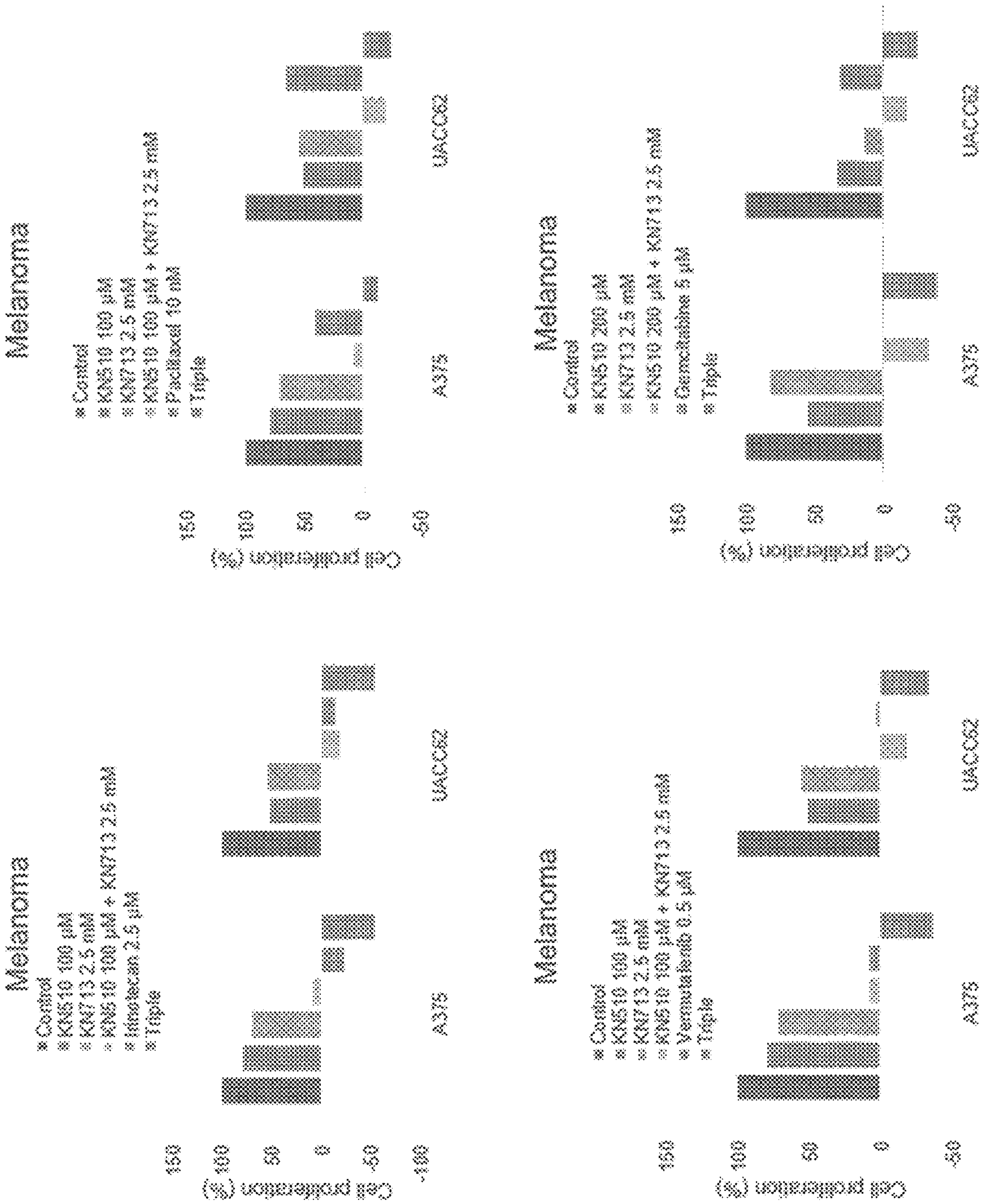
FIGS. 15*a* and 15*b* show the results of the analysis the effect of triple combination treatment of CAC inhibitor (KN510: omeprazole), ACAA inhibitor (KN713: trimetazidine) and anticancer drug on cell growth in a melanoma cell line.
Figure 15B:
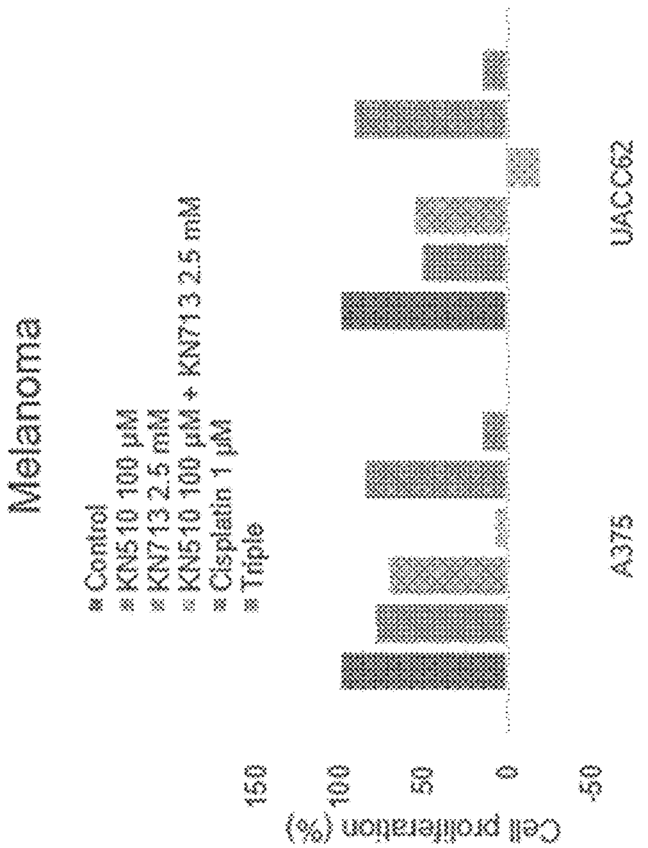
Figure 15B:
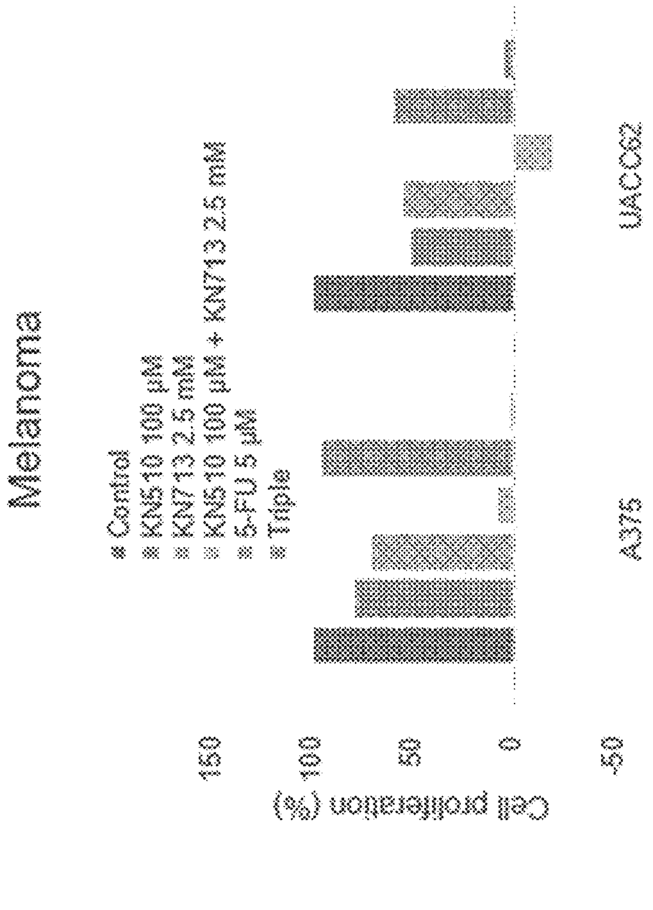
Figure 16A:
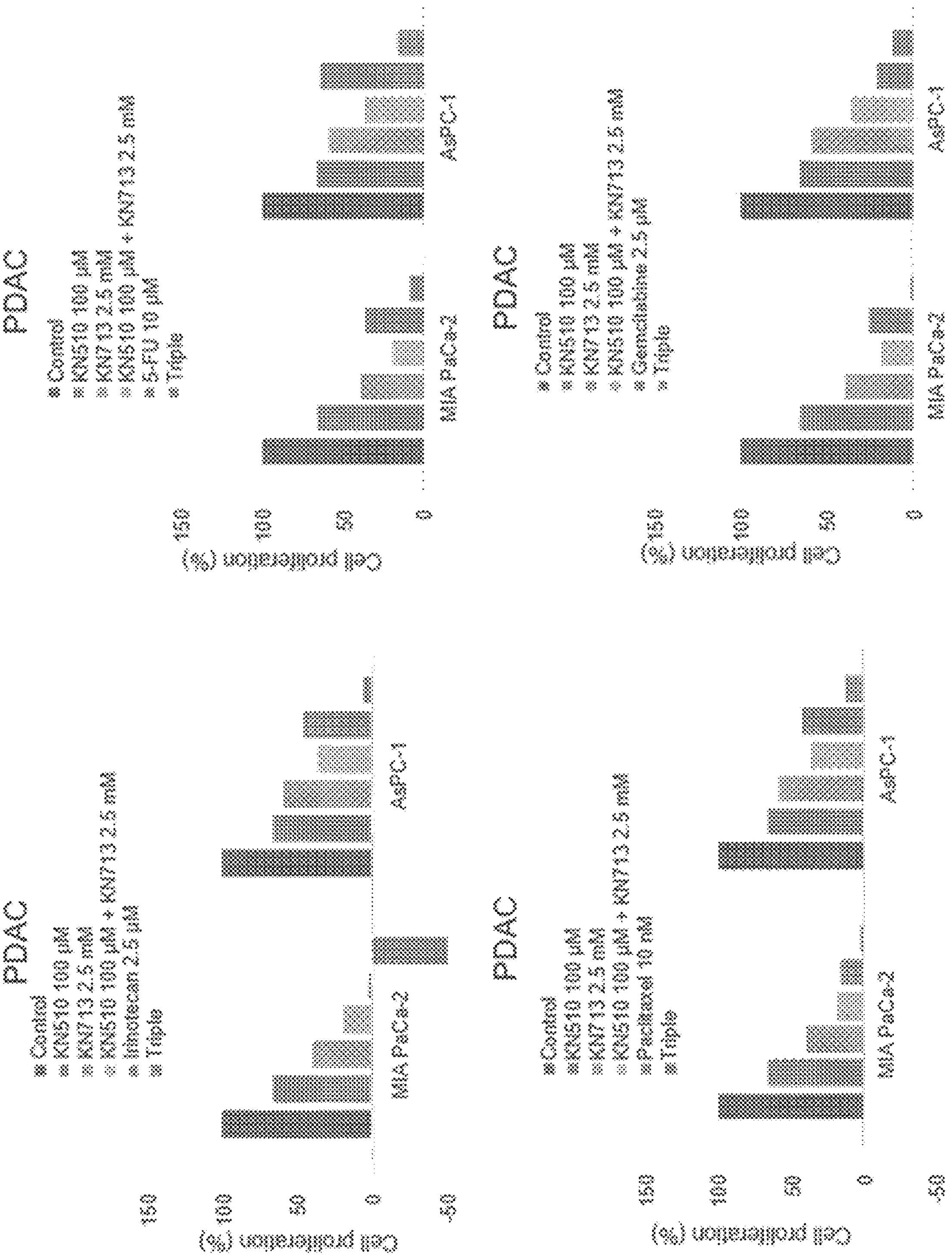
FIGS. 16*a* and 16*b* show the results of the analysis the effect of triple combination treatment of CAC inhibitor (KN510: omeprazole), ACAA inhibitor (KN713: trimetazidine) and anticancer drug on cell growth in a pancreatic cancer (PDAC) cell line.
Figure 16B:
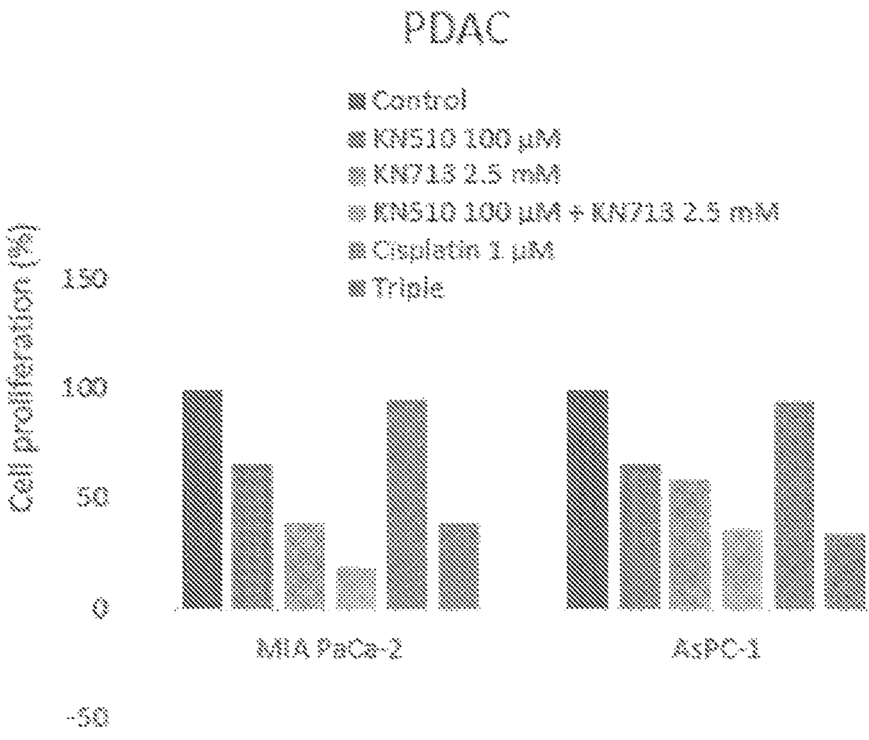
Figure 17A:
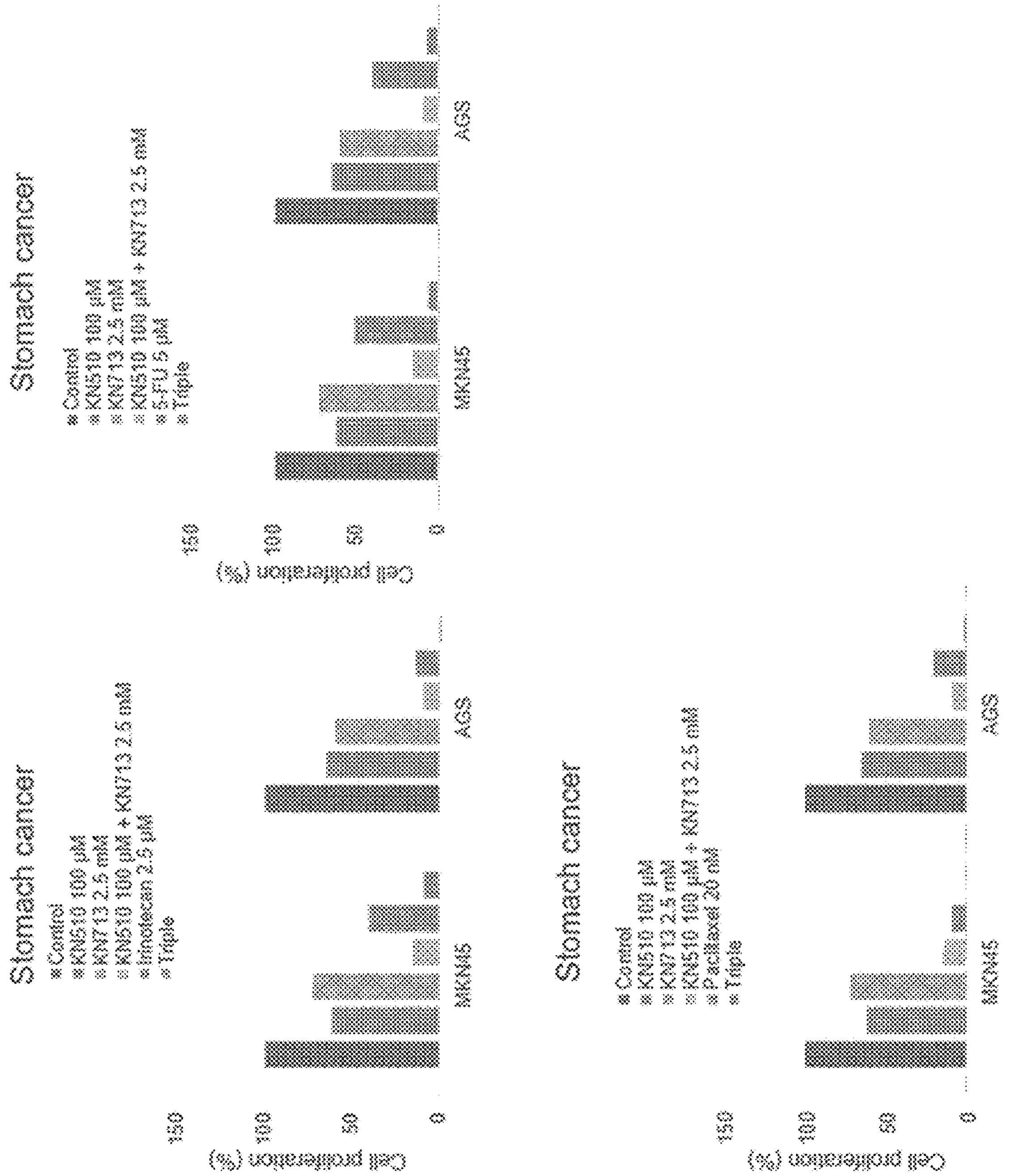
FIGS. 17*a* and 17*b* show the results of the analysis the effect of triple combination treatment of CAC inhibitor (KN510: omeprazole), ACAA inhibitor (KN713: trimetazidine) and anticancer drug on cell growth in a gastric cancer cell line.
Figure 17B:
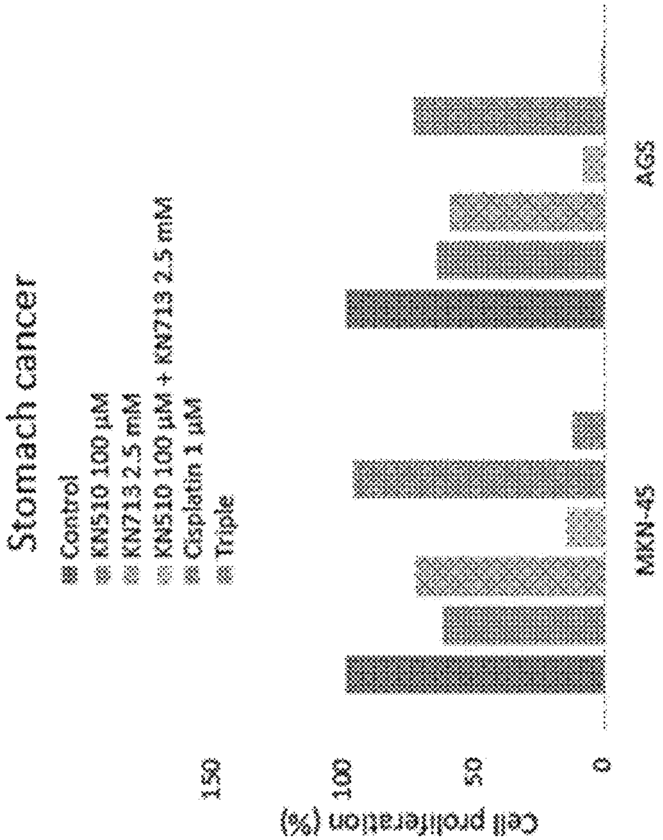
Figure 17B:
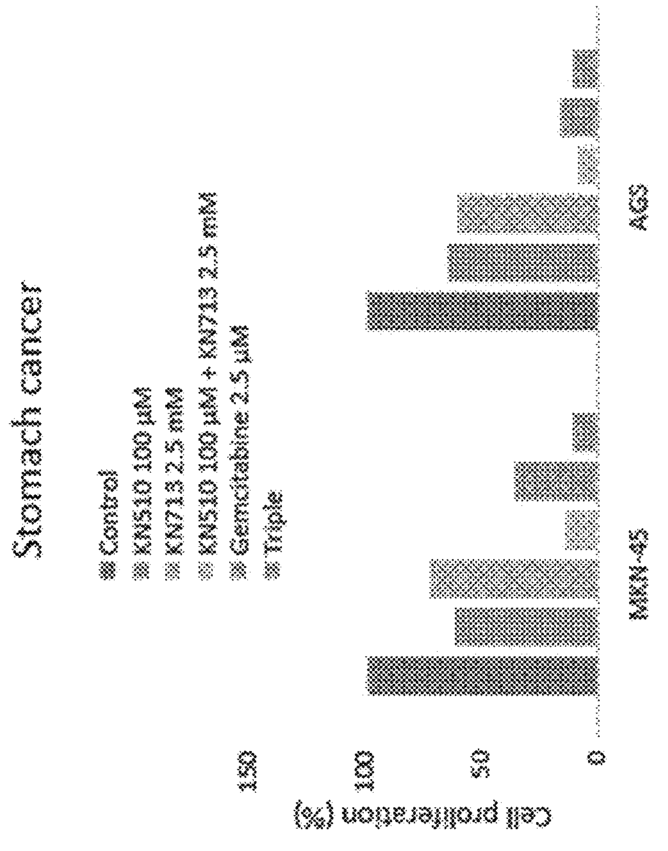
Figure 18A:
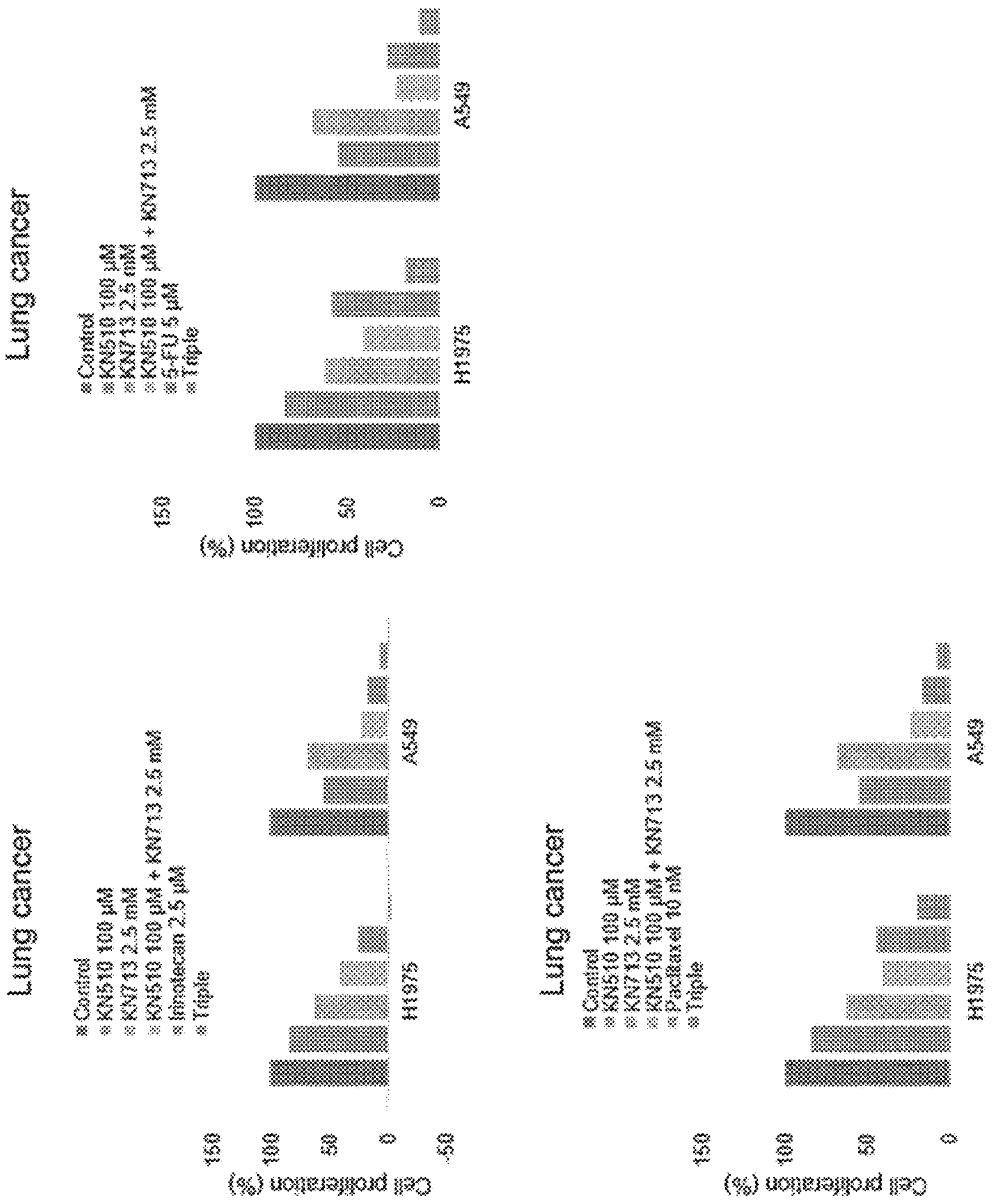
FIGS. 18*a* and 18*b* show the results of the analysis the effect of triple combination treatment of CAC inhibitor (KN510: omeprazole), ACAA inhibitor (KN713: trimetazidine) and anticancer drug on cell growth in a non-small cell lung cancer (NSCLC) cell line.
Figure 18B:
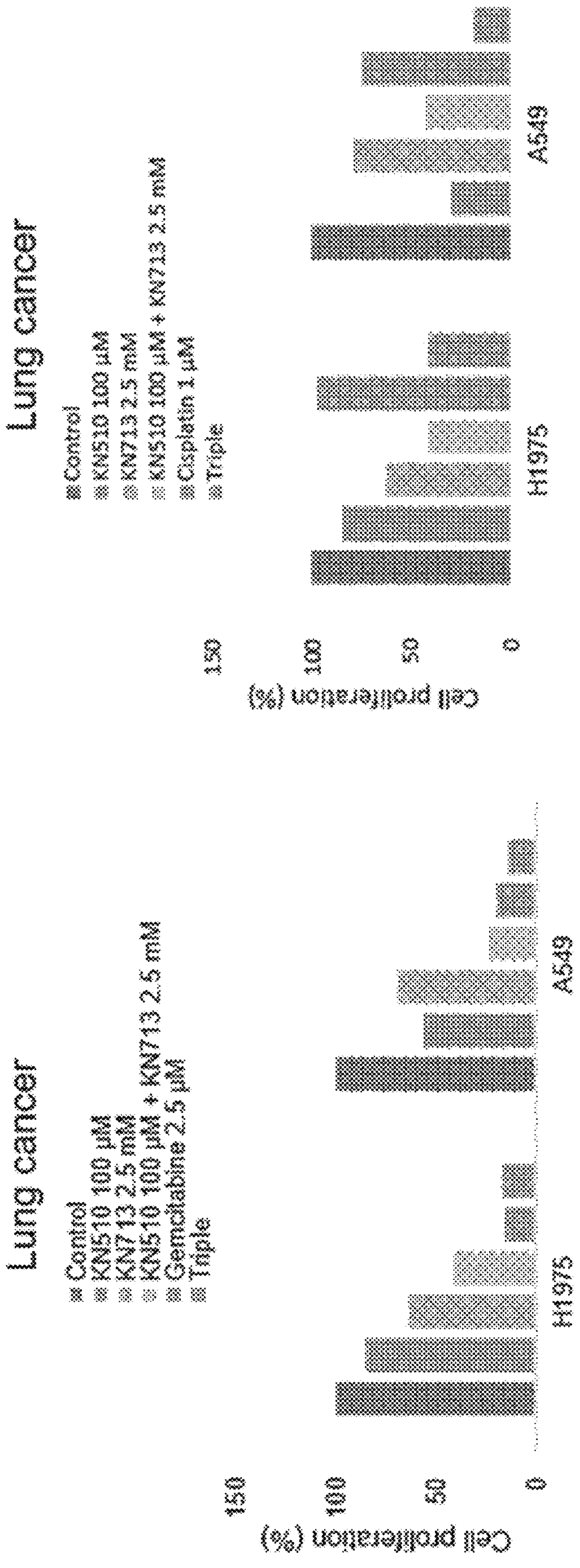

FIG. 7*d* and Table 9 show the results of analyzing the effect of the combined treatment of the CAC inhibitor KN511 (Lansoprazole) and the ACAA inhibitor KN715 (Ranolazine). This is the result of treatment with Control, KN511 50 μM alone, KN511 100 μM alone, KN715 200 μM alone, KN511 50 μM+KN715 200 μM (combination treatment), KN511 100 μM+KN715 200 μM (combination treatment) in pancreatic cancer cell lines for 48 hours. As shown in FIG. 7*d* and Table 9, it was confirmed that cell growth was significantly inhibited when the CAC inhibitor KN511 (Lansoprazole) and the ACAA inhibitor KN715 (Ranolazine) were co-treated.

TABLE 9

| | MIA PaCa-2 | Panc-1 | SW1990 | SU.86.86 | SNU213 | SNU324 | AsPC-1 | BxPC-3 |
|---|---|---|---|---|---|---|---|---|
| Control | 100.00 | 100.00 | 100.00 | 100.00 | 100.00 | 100.00 | 100.00 | 100.00 |
| KN511 50 μM | 68.24 | 39.30 | 7.49 | 31.47 | 49.55 | 17.09 | 38.02 | 41.39 |
| KN511 100 μM | 16.12 | 8.07 | −25.25 | 6.37 | 6.76 | 8.06 | 14.98 | −1.66 |
| KN715 200 μM | 65.15 | 7.04 | 22.15 | 63.92 | 12.22 | 23.63 | 57.91 | 45.76 |
| KN511 50 μM + KN715 200 μM | 25.16 | −18.92 | −34.22 | −1.40 | −26.62 | −6.68 | 14.73 | −9.98 |
| KN511 100 μM + KN715 200μM | −13.19 | −28.13 | −45.33 | −24.57 | −29.64 | −19.45 | −2.95 | −40.69 |

FIG. 7*e* and Table 10 show the results of analyzing the effect of the combined treatment of the CAC inhibitor KN512 (Pantoprazole) and the ACAA inhibitor KN715 (Ranolazine). This is the result of treatment with Control, KN512 100 μM alone, KN512 200 μM alone, KN715 200 μM alone, KN512 100 μM+KN715 200 μM (combination treatment), KN512 200 μM+KN715 200 μM (combination treatment) in pancreatic cancer cell lines for 48 hours. As shown in FIG. 7*e* and Table 10, it was confirmed that cell growth was significantly inhibited when the CAC inhibitor KN512 (Pantoprazole) and the ACAA inhibitor KN715 (Ranolazine) were co-treated.

TABLE 10

| | MIA PaCa-2 | Panc-1 | SW1990 | SU.86.86 | SNU213 | SNU324 | AsPC-1 | BxPC-3 |
|---|---|---|---|---|---|---|---|---|
| Control | 100.00 | 100.00 | 100.00 | 100.00 | 100.00 | 100.00 | 100.00 | 100.00 |
| KN512 100 μM | 66.74 | 57.01 | 73.00 | 70.59 | 59.49 | 74.13 | 71.27 | 49.52 |
| KN512 200 μM | 1.98 | 12.81 | 41.93 | 26.47 | 51.18 | 21.77 | 25.43 | −6.75 |
| KN715 200 μM | 73.29 | 20.30 | 74.06 | 73.38 | 18.98 | 27.45 | 63.15 | 59.04 |
| KN512 100 μM + KN715 200 μM | 32.10 | 2.98 | 37.25 | 30.34 | 27.76 | −2.21 | 42.93 | −0.12 |
| KN512 200 μM + KN715 200 μM | −12.33 | −14.10 | −5.15 | −0.13 | −6.03 | −6.34 | 21.15 | −28.09 |

Example 5

SRB Analysis 3

Through SRB analysis (n=3), the effect of triple combination treatment of a CAC inhibitor (KN510: omeprazole), ACAA inhibitor (KN713: trimetazidine) and other anticancer drug on cell growth in the cancer cells was analyzed. (see Table 11).

TABLE 11

| Panel Name | Cell Line Name | Positive/ Negative | Drugs |
|---|---|---|---|
| Colon Cancer | HT-29 | Positive | Paclitaxel, 5-fu |
| | COLO-205 | negative | Irinotecan, Gemcitabine, Cisplatin |
| Renal cell carcinoma | ACHN | Positive | 5-fu |
| | CAKI-1 | negative | Irinotecan, Gemcitabine, Cisplatin, Paclitaxel |
| Liver Cancer | SNU-449 | Positive | Paclitaxel, 5-fu |
| | Huh-7 | negative | Irinotecan, Gemcitabine, Cisplatin |
| Breast Cancer | BT-549 | Positive | Paclitaxel, Irinotecan |
| | MDA MB 231 | negative | Gemcitabine, Cisplatin, 5-fu |
| Ovarian Cancer | SK-OV-3 | Positive | paclitaxel |
| | OVCAR-3 | negative | Irinotecan, Gemcitabine, 5-fu, Cisplatin |
| Prostate Cancer | PC-3 | Positive | Paclitaxel, Irinotecan, Gemcitabine, 5-fu |
| | DU-145 | negative | Cisplatin |
| GBM | U87MG | Positive | Irinotecan, Paclitaxel, 5-fu |
| | T87G | negative | Gemcitabine, Cisplatin |

TABLE 11-continued

| Panel Name | Cell Line Name | Positive/ Negative | Drugs |
|---|---|---|---|
| melanoma | UACC62 | Positive | Paclitaxel, Irinotecan, Vermurafenib, Gemcitabine |
| | A375 | negative | Cisplatin, 5-fu |
| PDAC | MIA PaCa-2 | Positive | Paclitaxel, Irinotecan, Gemcitabine, 5-fu |
| | PANC-1 | negative | Cisplatin |
| Stomach Cancer | MKN-28 | Positive | Paclitaxel, Irinotecan, 5-fu |
| | AGS | negative | Gemcitabine, Cisplatin |
| NSCLC | A549 | Positive | Paclitaxel, Irinotecan, 5-fu |
| | H522 | negative | Gemcitabine, Cisplatin |

The SRB assay was performed as follows: each cell line (100 µl) was seeded into 96-well microtiter plates at densities ranging from 5,000 to 40,000 cells/well depending on the doubling time of each cell line. After 24 hours, drug (100 µl per well) was added to each well and the culture was incubated at 37° C. for 48 hours. Cells were then fixed in 50% TCA (50 µl per well) and plates were incubated at 4° C. for a minimum of 1 hour or a maximum of 3 hours. After that, the liquid was removed from the plate, then rinsed 5 times with water and dried for approximately 12-24 hours at room temperature (RT). After the fixed cells were stained with 0.4% SRB (100 µl per well) for 10 minutes at room temperature, the plates were washed 3 times with 1% glacial acetic acid and dried at room temperature for about 12-24 hours. SRB staining was dissolved in 10 mM Trizma base and absorbance was read at 515 nm. The effect of the drug was expressed as $GI_{50}$ (50% growth inhibition), TGI (total growth inhibition) or $LC_{50}$ (lethal concentration). $GI_{50}$ is the maximum concentration at the moment of 50% inhibition of cell proliferation and $IC_{50}$ is the concentration of the drug that inhibits the enzyme activity in vitro by 50% in this study.

As a result of the analysis, as shown in FIGS. 8 to 18 and Tables 12 to 67, when a triple combination of a Carnitine Acylcarnitine Carrier (CAC) inhibitor (KN510: omeprazole), a 3-ketoacyl CoA thiolase (ACAA) inhibitor (KN713: trimetazidine) and an anticancer agent was treated, it was confirmed that cell growth was significantly inhibited.

TABLE 12

| | COLO-205 | HCT-116 |
|---|---|---|
| Control | 100 | 100 |
| KN510 100 µM | 78.02787 | 79.64545 |
| KN713 2.5 mM | 31.61844 | 36.64073 |
| KN510 100 µM + KN713 2.5 mM | 12.62058 | 18.41602 |
| 5-FU 5 µM | −4.95713 | 14.61548 |
| Triple | −16.7738 | −1.58143 |

TABLE 13

| | COLO-205 | HCT-116 |
|---|---|---|
| Control | 100 | 100 |
| KN510 100 µM | 78.02787 | 79.64545 |
| KN713 2.5 mM | 31.61844 | 36.64073 |
| KN510 100 µM + KN713 2.5 mM | 12.62058 | 18.41602 |

TABLE 13-continued

| | COLO-205 | HCT-116 |
|---|---|---|
| Paclitaxel 10 nM | −8.62808 | 15.07461 |
| Triple | −29.0997 | 1.415636 |

TABLE 14

| | COLO-205 | HCT-116 |
|---|---|---|
| Control | 100 | 100 |
| KN510 100 µM | 78.02787 | 79.64545 |
| KN713 2.5 mM | 31.61844 | 36.64073 |
| KN510 100 µM + KN713 2.5 mM | 12.62058 | 18.41602 |
| Irinotecan 2.5 µM | 10.02144 | −0.34434 |
| Triple | −24.8928 | −1.4539 |

TABLE 15

| | COLO-205 | HCT-116 |
|---|---|---|
| Control | 100 | 100 |
| KN510 100 µM | 78.02787 | 79.64545 |
| KN713 2.5 mM | 31.61844 | 36.64073 |
| KN510 100 µM + KN713 2.5 mM | 12.62058 | 18.41602 |
| Gemcitabine 2.5 µM | 6.028939 | 3.787782 |
| Triple | −6.8328 | 1.058538 |

TABLE 16

| | COLO-205 | HCT-116 |
|---|---|---|
| Control | 100 | 100 |
| KN510 100 µM | 78.02787 | 79.64545 |
| KN713 2.5 mM | 31.61844 | 36.64073 |
| KN510 100 µM + KN713 2.5 mM | 12.62058 | 18.41602 |
| Cisplatin 1 µM | 83.44051 | 100.5484 |
| Triple | 10.36977 | 21.77018 |

TABLE 17

| | ACHN | Caki-1 |
|---|---|---|
| Control | 100 | 100 |
| KN510 100 µM | 61.16778 | 102.1283 |
| KN713 2.5 mM | 65.67007 | 47.58285 |
| KN510 100 µM + KN713 2.5 mM | 22.828 | 40.01216 |
| 5-FU 5 µM | 26.38058 | 59.41016 |
| Triple | −23.4611 | 29.8267 |

TABLE 18

| | ACHN | Caki-1 |
|---|---|---|
| Control | 100 | 100 |
| KN510 100 µM | 61.16778 | 102.1283 |
| KN713 2.5 mM | 65.67007 | 47.58285 |
| KN510 100 µM + KN713 2.5 mM | 22.828 | 40.01216 |
| Irinotecan 2.5 µM | −43.8973 | 22.65126 |
| Triple | −33.0988 | 22.37762 |

TABLE 19

| | ACHN | Caki-1 |
|---|---|---|
| Control | 100 | 100 |
| KN510 100 µM | 61.16778 | 102.1283 |

TABLE 19-continued

| | ACHN | Caki-1 |
|---|---|---|
| KN713 2.5 mM | 65.67007 | 47.58285 |
| KN510 100 µM + KN713 2.5 mM | 22.828 | 40.01216 |
| Cisplatin 1 µM | 118.1147 | 113.4691 |
| Triple | 23.98874 | 49.16388 |

TABLE 20

| | ACHN | Caki-1 |
|---|---|---|
| Control | 100 | 100 |
| KN510 100 µM | 61.16778 | 102.1283 |
| KN713 2.5 mM | 65.67007 | 47.58285 |
| KN510 100 µM + KN713 2.5 mM | 22.828 | 40.01216 |
| Paclitaxel 10 nM | 105.2409 | 128.124 |
| Triple | 8.758354 | 62.66342 |

TABLE 21

| | ACHN | Caki-1 |
|---|---|---|
| Control | 100 | 100 |
| KN510 100 µM | 61.16778 | 102.1283 |
| KN713 2.5 mM | 65.67007 | 47.58285 |
| KN510 100 µM + KN713 2.5 mM | 22.828 | 40.01216 |
| Gemcitabine 2.5 µM | −47.9775 | 28.94497 |
| Triple | −46.9926 | 25.87413 |

TABLE 22

| | Huh-7 | SK-hep-1 |
|---|---|---|
| Control | 100 | 100 |
| KN510 100 µM | 77.72926 | 60.37567 |
| KN713 2.5 mM | 52.08983 | 157.7818 |
| KN510 100 µM + KN713 2.5 mM | 22.39551 | 48.12165 |
| 5-FU 5 µM | 34.9345 | 149.7317 |
| Triple | −6.36307 | 19.0966 |

TABLE 23

| | Huh-7 | SK-hep-1 |
|---|---|---|
| Control | 100 | 100 |
| KN510 100 µM | 77.72926 | 60.37567 |
| KN713 2.5 mM | 52.08983 | 157.7818 |
| KN510 100 µM + KN713 2.5 mM | 22.39551 | 48.12165 |
| Paclitaxel 10 µM | 63.00686 | 78.75671 |
| Triple | 10.79226 | 21.95886 |

TABLE 24

| | Huh-7 | SK-hep-1 |
|---|---|---|
| Control | 100 | 100 |
| KN510 100 µM | 77.72926 | 60.37567 |
| KN713 2.5 mM | 52.08983 | 157.7818 |
| KN510 100 µM + KN713 2.5 mM | 22.39551 | 48.12165 |
| Irinotecan 2.5 µM | 15.47099 | −15.5188 |
| Triple | −5.55209 | 4.695886 |

TABLE 25

| | Huh-7 | SK-hep-1 |
|---|---|---|
| Control | 100 | 100 |
| KN510 100 µM | 77.72926 | 60.37567 |
| KN713 2.5 mM | 52.08983 | 157.7818 |
| KN510 100 µM + KN713 2.5 mM | 22.39551 | 48.12165 |
| Cisplatin 1 µM | 66.68746 | 136.3148 |
| Triple | 23.95508 | 75.17889 |

TABLE 26

| | Huh-7 | SK-hep-1 |
|---|---|---|
| Control | 100 | 100 |
| KN510 100 µM | 77.72926 | 60.37567 |
| KN713 2.5 mM | 52.08983 | 157.7818 |
| KN510 100 µM + KN713 2.5 mM | 22.39551 | 48.12165 |
| Gemcitabine 2.5 µM | 33.12539 | 22.18247 |
| Triple | 23.58079 | 24.86583 |

TABLE 27

| | MCF7 | MDA-MB-231 |
|---|---|---|
| Control | 100 | 100 |
| KN510 100 µM | 70.29813 | 86.99128 |
| KN713 2.5 mM | 60.36329 | 74.5469 |
| KN510 100 µM + KN713 2.5 mM | 24.26251 | 65.57537 |
| Irinotecan 2.5 µM | 7.426893 | 78.25128 |
| Triple | −1.43548 | 41.26542 |

TABLE 28

| | MCF7 | MDA-MB-231 |
|---|---|---|
| Control | 100 | 100 |
| KN510 100 µM | 70.29813 | 86.99128 |
| KN713 2.5 mM | 60.36329 | 74.5469 |
| KN510 100 µM + KN713 2.5 mM | 24.26251 | 65.57537 |
| Paclitaxel 10 µM | 17.28189 | 70.48077 |
| Triple | 3.525956 | 32.77141 |

TABLE 29

| | MCF7 | MDA-MB-231 |
|---|---|---|
| Control | 100 | 100 |
| KN510 100 µM | 70.29813 | 86.99128 |
| KN713 2.5 mM | 60.36329 | 74.5469 |
| KN510 100 µM + KN713 2.5 mM | 24.26251 | 65.57537 |
| 5-FU 5 µM | 11.29361 | 73.95362 |
| Triple | 6.696893 | 63.12991 |

TABLE 30

| | MCF7 | MDA-MB-231 |
|---|---|---|
| Control | 100 | 100 |
| KN510 100 µM | 70.29813 | 86.99128 |
| KN713 2.5 mM | 60.36329 | 74.5469 |
| KN510 100 µM + KN713 2.5 mM | 24.26251 | 65.57537 |
| Cisplatin 1 µM | 70.82282 | 93.90804 |
| Triple | 22.84814 | 68.07872 |

TABLE 31

| | MCF7 | MDA-MB-231 |
|---|---|---|
| Control | 100 | 100 |
| KN510 100 μM | 70.29813 | 86.99128 |
| KN713 2.5 mM | 60.36329 | 74.5469 |
| KN510 100 μM + KN713 2.5 mM | 24.26251 | 65.57537 |
| Gemcitabine 2.5 μM | 12.30877 | 65.05444 |
| Triple | 5.214081 | 61.3356 |

TABLE 32

| | OVCAR-8 | SK-OV-3 |
|---|---|---|
| Control | 100 | 100 |
| KN510 100 μM | 68.74947 | 85.05874 |
| KN713 2.5 mM | 72.86018 | 83.37182 |
| KN510 100 μM + KN713 2.5 mM | 30.75373 | 61.36158 |
| Paclitaxel 10 μM | 76.60752 | 62.40586 |
| Triple | 21.10149 | 29.31017 |

TABLE 33

| | OVCAR-8 | SK-OV-3 |
|---|---|---|
| Control | 100 | 100 |
| KN510 100 μM | 68.74947 | 85.05874 |
| KN713 2.5 mM | 72.86018 | 83.37182 |
| KN510 100 μM + KN713 2.5 mM | 30.75373 | 61.36158 |
| Irinotecan 2.5 μM | 36.34067 | 13.56562 |
| Triple | 19.489 | 18.22472 |

TABLE 34

| | OVCAR-8 | SK-OV-3 |
|---|---|---|
| Control | 100 | 100 |
| KN510 100 μM | 68.74947 | 85.05874 |
| KN713 2.5 mM | 72.86018 | 83.37182 |
| KN510 100 μM + KN713 2.5 mM | 30.75373 | 61.36158 |
| Gemcitabine 2.5 μM | 21.23776 | 24.20926 |
| Triple | 15.37828 | 31.76022 |

TABLE 35

| | OVCAR-8 | SK-OV-3 |
|---|---|---|
| Control | 100 | 100 |
| KN510 100 μM | 68.74947 | 85.05874 |
| KN713 2.5 mM | 72.86018 | 83.37182 |
| KN510 100 μM + KN713 2.5 mM | 30.75373 | 61.36158 |
| 5-FU 5 μM | 77.83392 | 80.76112 |
| Triple | 25.30305 | 61.56241 |

TABLE 36

| | OVCAR-8 | SK-OV-3 |
|---|---|---|
| Control | 100 | 100 |
| KN510 100 μM | 68.74947 | 85.05874 |
| KN713 2.5 mM | 72.86018 | 83.37182 |
| KN510 100 μM + KN713 2.5 mM | 30.75373 | 61.36158 |
| Cisplatin 1 μM | 84.76082 | 75.0979 |
| Triple | 29.16395 | 64.57476 |

TABLE 37

| | PC-3 | DU145 |
|---|---|---|
| Control | 100 | 100 |
| KN510 100 μM | 59.63027 | 76.71094 |
| KN713 2.5 mM | 45.05589 | 55.68388 |
| KN510 100 μM + KN713 2.5 mM | 22.26999 | 40.39147 |
| Irinotecan 5 μM | 37.70421 | 28.60357 |
| Triple | 14.25193 | 7.449075 |

TABLE 38

| | PC-3 | DU145 |
|---|---|---|
| Control | 100 | 100 |
| KN510 100 μM | 59.63027 | 76.71094 |
| KN713 2.5 mM | 45.05589 | 55.68388 |
| KN510 100 μM + KN713 2.5 mM | 22.26999 | 40.39147 |
| 5-FU 5 μM | 51.6552 | 59.63442 |
| Triple | 13.04815 | 20.28833 |

TABLE 39

| | PC-3 | DU145 |
|---|---|---|
| Control | 100 | 100 |
| KN510 100 μM | 59.63027 | 76.71094 |
| KN713 2.5 mM | 45.05589 | 55.68388 |
| KN510 100 μM + KN713 2.5 mM | 22.26999 | 40.39147 |
| Paclitaxel 10 nM | 47.85039 | 46.381 |
| Triple | 15.86414 | 13.40674 |

TABLE 40

| | PC-3 | DU145 |
|---|---|---|
| Control | 100 | 100 |
| KN510 100 μM | 59.63027 | 76.71094 |
| KN713 2.5 mM | 45.05589 | 55.68388 |
| KN510 100 μM + KN713 2.5 mM | 22.26999 | 40.39147 |
| Gemcitabine 5 μM | 48.0 | 45.32964 |
| Triple | 9.479794 | 0.2489 |

TABLE 41

| | PC-3 | DU145 |
|---|---|---|
| Control | 100 | 100 |
| KN510 100 μM | 59.63027 | 76.71094 |
| KN713 2.5 mM | 45.05589 | 55.68388 |
| KN510 100 μM + KN713 2.5 mM | 22.26999 | 40.39147 |
| Cisplatin 1 μM | 67.15391 | 60.84506 |
| Triple | 21.15219 | 35.48516 |

TABLE 42

| | T87G | U87MG |
|---|---|---|
| Control | 100.00 | 100.00 |
| KN510 100 μM | 67.87 | 84.15 |
| KN713 2.5 mM | 59.89 | 66.40 |
| KN510 100 μM + KN713 2.5 mM | 15.71 | 29.58 |
| Irinotecan 2.5 μM | 71.53 | 6.31 |
| Triple | −11.41 | −23.93 |

TABLE 43

| | T87G | U87MG |
|---|---|---|
| Control | 100.00 | 100.00 |
| KN510 100 μM | 67.87 | 84.15 |
| KN713 2.5 mM | 59.89 | 66.40 |
| KN510 100 μM + KN713 2.5 mM | 15.71 | 29.58 |
| Paclitaxel 10 nM | 56.70 | 28.87 |
| Triple | −12.63 | 14.18 |

TABLE 44

| | T87G | U87MG |
|---|---|---|
| Control | 100.00 | 100.00 |
| KN510 100 μM | 67.87 | 84.15 |
| KN713 2.5 mM | 59.89 | 66.40 |
| KN510 100 μM + KN713 2.5 mM | 15.71 | 29.58 |
| Paclitaxel 10 nM | 56.70 | 28.87 |
| Triple | −12.63 | 14.18 |

TABLE 45

| | T87G | U87MG |
|---|---|---|
| Control | 100.00 | 100.00 |
| KN510 100 μM | 67.87 | 84.15 |
| KN713 2.5 mM | 59.89 | 66.40 |
| KN510 100 μM + KN713 2.5 mM | 15.71 | 29.58 |
| Gemcitabine 5 μM | 53.69 | 3.67 |
| Triple | 22.23 | 10.51 |

TABLE 46

| | T87G | U87MG |
|---|---|---|
| Control | 100.00 | 100.00 |
| KN510 100 μM | 67.87 | 84.15 |
| KN713 2.5 mM | 59.89 | 66.40 |
| KN510 100 μM + KN713 2.5 mM | 15.71 | 29.58 |
| Cisplatin 1 μM | 120.49 | 87.30 |
| Triple | 19.50 | 37.97 |

TABLE 47

| | A375 | UACC62 |
|---|---|---|
| Control | 100.00 | 100.00 |
| KN510 100 μM | 79.18 | 50.83 |
| KN713 2.5 mM | 70.33 | 54.65 |
| KN510 100 μM + KN713 2.5 mM | 7.28 | −19.72 |
| Irinotecan 2.5 μM | −23.32 | −13.35 |
| Triple | −53.75 | −53.85 |

TABLE 48

| | A375 | UACC62 |
|---|---|---|
| Control | 100.00 | 100.00 |
| KN510 100 μM | 79.18 | 50.83 |
| KN713 2.5 mM | 70.33 | 54.65 |
| KN510 100 μM + KN713 2.5 mM | 7.28 | −19.72 |
| Paclitaxel 10 nM | 40.20 | 65.90 |
| Triple | −13.83 | −24.49 |

TABLE 49

| | A375 | UACC62 |
|---|---|---|
| Control | 100.00 | 100.00 |
| KN510 100 μM | 79.18 | 50.83 |
| KN713 2.5 mM | 70.33 | 54.65 |
| KN510 100 μM + KN713 2.5 mM | 7.28 | −19.72 |
| Vermutafenib 0.5 μM | 7.77 | 2.10 |
| Triple | −37.35 | −34.57 |

TABLE 50

| | A375 | UACC62 |
|---|---|---|
| Control | 100.00 | 100.00 |
| KN510 100 μM | 79.18 | 50.83 |
| KN713 2.5 mM | 70.33 | 54.65 |
| KN510 100 μM + KN713 2.5 mM | 7.28 | −19.72 |
| Gemcitabine 5 μM | 25.12 | 31.60 |
| Triple | 2.61 | 6.30 |

TABLE 51

| | A375 | UACC62 |
|---|---|---|
| Control | 100.00 | 100.00 |
| KN510 100 μM | 79.18 | 50.83 |
| KN713 2.5 mM | 70.33 | 54.65 |
| KN510 100 μM + KN713 2.5 mM | 7.28 | −19.72 |
| 5-FU 5 μM | 95.91 | 59.14 |
| Triple | 0.75 | 4.10 |

TABLE 52

| | A375 | UACC62 |
|---|---|---|
| Control | 100.00 | 100.00 |
| KN510 100 μM | 79.18 | 50.83 |
| KN713 2.5 mM | 70.33 | 54.65 |
| KN510 100 μM + KN713 2.5 mM | 7.28 | −19.72 |
| Cisplatin 1 μM | 85.06 | 91.68 |
| Triple | 14.69 | 13.56 |

TABLE 53

| | MIA PaCa-2 | AsPC-1 |
|---|---|---|
| Control | 100 | 100 |
| KN510 100 μM | 65.94065 | 65.83338 |
| KN713 2.5 mM | 39.45194 | 58.70792 |
| KN510 100 μM + KN713 2.5 mM | 18.72939 | 35.89975 |
| Irinotecan 2.5 μM | 2.589799 | 45.74677 |
| Triple | −51.3477 | 6.120637 |

TABLE 54

| | MIA PaCa-2 | AsPC-1 |
|---|---|---|
| Control | 100 | 100 |
| KN510 100 μM | 65.94065 | 65.83338 |
| KN713 2.5 mM | 39.45194 | 58.70792 |
| KN510 100 μM + KN713 2.5 mM | 18.72939 | 35.89975 |
| 5-FU 10 μM | 36.7557 | 64.54196 |
| Triple | 8.758154 | 15.80494 |

TABLE 55

| | MIA PaCa-2 | AsPC-1 |
|---|---|---|
| Control | 100 | 100 |
| KN510 100 μM | 65.94065 | 65.83338 |
| KN713 2.5 mM | 39.45194 | 58.70792 |
| KN510 100 μM + KN713 2.5 mM | 18.72939 | 35.89975 |
| Paclitaxel 10 nM | 16.40365 | 41.94357 |
| Triple | 2.382746 | 13.34487 |

TABLE 56

| | MIA PaCa-2 | AsPC-1 |
|---|---|---|
| Control | 100 | 100 |
| KN510 100 μM | 65.94065 | 65.83338 |
| KN713 2.5 mM | 39.45194 | 58.70792 |
| KN510 100 μM + KN713 2.5 mM | 18.72939 | 35.89975 |
| Gemcitabine 2.5 μM | 25.9 | 20.82769 |
| Triple | 1.057626 | 11.62992 |

TABLE 57

| | MIA PaCa-2 | AsPC-1 |
|---|---|---|
| Control | 100 | 100 |
| KN510 100 μM | 65.94065 | 65.83338 |
| KN713 2.5 mM | 39.45194 | 58.70792 |
| KN510 100 μM + KN713 2.5 mM | 18.72939 | 35.89975 |
| Cisplatin 1 μM | 95.90651 | 94.83738 |
| Triple | 39.30893 | 34.37957 |

TABLE 58

| | MKN45 | AGS |
|---|---|---|
| Control | 100 | 100 |
| KN510 100 μM | 62.39428 | 65.05158 |
| KN713 2.5 mM | 72.84838 | 60.34412 |
| KN510 100 μM + KN713 2.5 mM | 14.8862 | 9.068564 |
| Irinotecan 2.5 μM | 40.94276 | 13.57683 |
| Triple | 9.158589 | −14.6287 |

TABLE 59

| | MKN45 | AGS |
|---|---|---|
| Control | 100 | 100 |
| KN510 100 μM | 62.39428 | 65.05158 |
| KN713 2.5 mM | 72.84838 | 60.34412 |
| KN510 100 μM + KN713 2.5 mM | 14.8862 | 9.068564 |
| 5-FU 5 μM | 51.02643 | 39.83588 |
| Triple | 5.797369 | 6.497184 |

TABLE 60

| | MKN-45 | AGS |
|---|---|---|
| Control | 100 | 100 |
| KN510 100 μM | 62.39428 | 65.05158 |
| KN713 2.5 mM | 72.84838 | 60.34412 |
| KN510 100 μM + KN713 2.5 mM | 14.8862 | 9.068564 |
| Paclitaxel 20 nM | 8.846056 | 20.3903 |
| Triple | −1.27703 | 1.341407 |

TABLE 61

| | MKN-45 | AGS |
|---|---|---|
| Control | 100 | 100 |
| KN510 100 μM | 62.39428 | 65.05158 |
| KN713 2.5 mM | 72.84838 | 60.34412 |
| KN510 100 μM + KN713 2.5 mM | 14.8862 | 9.068564 |
| Gemcitabine 2.5 μM | 36.14287 | 15.95099 |
| Triple | 10.64648 | 10.49868 |

TABLE 62

| | MKN-45 | AGS |
|---|---|---|
| Control | 100 | 100 |
| KN510 100 μM | 62.39428 | 65.05158 |
| KN713 2.5 mM | 72.84838 | 60.34412 |
| KN510 100 μM + KN713 2.5 mM | 14.8862 | 9.068564 |
| Cisplatin 1 μM | 96.28497 | 74.02414 |
| Triple | 11.81218 | 0.859212 |

TABLE 63

| | H1975 | A549 |
|---|---|---|
| Control | 100 | 100 |
| KN510 100 μM | 84.1319 | 55.4 |
| KN713 2.5 mM | 62.57796 | 68.8 |
| KN510 100 μM + KN713 2.5 mM | 41.60139 | 23 |
| Irinotecan 2.5 μM | 25.70731 | 17.6 |
| Triple | −0.43811 | 7.4 |

TABLE 64

| | H1975 | A549 |
|---|---|---|
| Control | 100 | 100 |
| KN510 100 μM | 84.1319 | 55.4 |
| KN713 2.5 mM | 62.57796 | 68.8 |
| KN510 100 μM + KN713 2.5 mM | 41.60139 | 23 |
| 5-FU5 μM | 58.333 | 28.5 |
| Triple | 18.28156 | 10.7231 |

TABLE 65

| | H1975 | A549 |
|---|---|---|
| Control | 100 | 100 |
| KN510 100 μM | 84.1319 | 55.4 |
| KN713 2.5 mM | 62.57796 | 68.8 |
| KN510 100 μM + KN713 2.5 mM | 41.60139 | 24.85251 |
| Paclitaxel 10 nM | 45.05661 | 17.6 |
| Triple | 20.07201 | 8.104702 |

TABLE 66

| | H1975 | A549 |
|---|---|---|
| Control | 100 | 100 |
| KN510 100 μM | 84.1319 | 55.4 |
| KN713 2.5 mM | 62.57796 | 68.8 |
| KN510 100 μM + KN713 2.5 mM | 41.60139 | 23 |
| Gemcitabine 2.5 μM | 16.13815 | 19.65176 |
| Triple | 16.7865 | 14.31353 |

TABLE 67

| | H1975 | A549 |
|---|---|---|
| Control | 100 | 100 |
| KN510 100 μM | 84.1319 | 30.1 |
| KN713 2.5 mM | 62.57796 | 79.2 |
| KN510 100 μM + KN713 2.5 mM | 41.60139 | 42.4 |
| Cisplatin 1 μM | 97.49364 | 75.07433 |
| Triple | 41.74869 | 18.31467 |

The invention claimed is:

1. A pharmaceutical composition for treating pancreatic cancer, comprising a 3-ketoacyl CoA thiolase (ACAA) inhibitor and a carnitine acylcarnitine carrier (CAC) inhibitor, wherein the ACAA inhibitor is trimetazidine, ranolazine, or a pharmaceutically acceptable salt thereof, and wherein the CAC inhibitor is omeprazole, lansoprazole, pantoprazole, or a pharmaceutically acceptable salt thereof.

2. The pharmaceutical composition according to claim 1, wherein the ACAA inhibitor and the CAC inhibitor are contained in a concentration ratio of 1:100 to 100:1.

3. The pharmaceutical composition according to claim 1, wherein the ACAA inhibitor and the CAC inhibitor are administered sequentially or simultaneously.

4. The pharmaceutical composition according to claim 1, further comprising an additional anticancer agent, wherein the additional anticancer agent is at least one selected from the group consisting of irinotecan, paclitaxel, capecitabine (5-fu), and a pharmaceutically acceptable salt thereof.

5. An anticancer adjuvant for treating pancreatic cancer, comprising a 3-ketoacyl CoA thiolase (ACAA) inhibitor and a carnitine acylcarnitine carrier inhibitor, wherein the ACAA inhibitor is trimetazidine, ranolazine, or a pharmaceutically acceptable salt thereof, and wherein the CAC inhibitor is omeprazole, lansoprazole, pantoprazole, or a pharmaceutically acceptable salt thereof.

6. The anticancer adjuvant according to claim 5, wherein the ACAA inhibitor and the CAC inhibitor are included in a concentration ratio of 1:100 to 100:1.

7. The anticancer adjuvant according to claim 5, wherein the ACAA inhibitor and the CAC inhibitor are administered sequentially or simultaneously.

8. The anticancer adjuvant according to claim 5, further comprising an additional anticancer agent, wherein the additional anticancer agent is at least one selected from the group consisting of irinotecan, paclitaxel, capecitabine (5-fu), and a pharmaceutically acceptable salt thereof.

9. A method for treating pancreatic cancer, the method comprising:

administering or taking a composition comprising a 3-ketoacyl CoA thiolase (ACAA) inhibitor and a carnitine acylcarnitine carrier (CAC) inhibitor as an active ingredient to an individual, wherein the ACAA inhibitor is trimetazidine, ranolazine, or a pharmaceutically acceptable salt thereof, and wherein the CAC inhibitor is omeprazole, lansoprazole, pantoprazole, or a pharmaceutically acceptable salt thereof.

* * * * *